United States Patent
Lefkowitz et al.

(10) Patent No.: US 6,841,663 B2
(45) Date of Patent: Jan. 11, 2005

(54) CHEMICAL ARRAYS

(75) Inventors: Steven M. Lefkowitz, Branford, CT (US); Michel G. M. Perbost, Bethany, CT (US); Roy H. Kanemoto, Palo Alto, CA (US); Carol T. Schembri, San Mateo, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 468 days.

(21) Appl. No.: 10/032,608

(22) Filed: Oct. 18, 2001

(65) Prior Publication Data

US 2003/0077380 A1 Apr. 24, 2003

(51) Int. Cl.[7] .................. C07H 21/00; C07H 21/02
(52) U.S. Cl. ............................................. 536/25.3
(58) Field of Search ...................... 435/6, 91.1, 7.1, 435/287.1, 41, 4; 436/518, 43; 536/25.3; 530/300

(56) References Cited

U.S. PATENT DOCUMENTS

| | | |
|---|---|---|
| 4,071,315 A | 1/1978 | Chateau |
| 5,429,807 A | 7/1995 | Matson et al. |
| 5,508,200 A | 4/1996 | Tiffany et al. |
| 5,550,063 A | 8/1996 | Bogart |
| 5,552,272 A | 9/1996 | Bogart |
| 5,629,214 A | 5/1997 | Crosby |
| 5,658,802 A | 8/1997 | Hayes et al. |
| 5,847,105 A | 12/1998 | Baldeschwieler et al. |
| 5,981,733 A * | 11/1999 | Gamble et al. ............ 536/25.3 |
| 6,008,892 A | 12/1999 | Kain et al. |
| 6,060,237 A | 5/2000 | Nygren et al. |
| 6,171,797 B1 | 1/2001 | Perbost |
| 6,177,990 B1 | 1/2001 | Kain et al. |
| 6,599,693 B1 * | 7/2003 | Webb ............................ 435/4 |
| 2002/0132261 A1 * | 9/2002 | Dorsel et al. .................. 435/6 |
| 2003/0054176 A1 * | 3/2003 | Pantano et al. ............ 428/429 |

FOREIGN PATENT DOCUMENTS

| | | |
|---|---|---|
| EP | 0 385 433 | 9/1990 |
| WO | WO 91/04483 | 4/1991 |
| WO | WO 95/25116 | 9/1995 |
| WO | WO 96/35971 | 11/1996 |
| WO | WO 99/54736 | 10/1999 |
| WO | WO 00/15653 | 3/2000 |
| WO | WP 01/36958 | 5/2001 |
| WO | WO 01/66244 | 9/2001 |

* cited by examiner

*Primary Examiner*—Kenneth R. Horlick
*Assistant Examiner*—Heather G. Calamita
(74) *Attorney, Agent, or Firm*—Gordon Steward

(57) ABSTRACT

Methods, apparatus, and computer program products to form arrays of polymers each having a pattern of features on a surface of a flexible elongated web, comprising. In a method polymers or their precursor units are applied at an application station to the surface. Multiple features are covered at a reagent station with a continuous volume of reagent which chemically reacts with precursors or the web. The flexible elongated web is driven in a lengthwise direction through the application station. This sequence may be repeated as needed to form the arrays along the web. Also provided is a method preparing a surface of a flexible elongated web to receive a biopolymer array.

43 Claims, 11 Drawing Sheets

CHEMICAL ARRAYS

FIELD OF THE INVENTION

This invention relates to arrays, such as polynucleotide arrays (for example, DNA arrays), which are useful in diagnostic, screening, gene expression analysis, and other applications.

BACKGROUND OF THE INVENTION

In the following discussion and throughout the present application, no cited reference is admitted to be prior art to the present application.

Arrays such as polynucleotide or protein arrays (for example, DNA or RNA arrays), are known and are used, for example, as diagnostic or screening tools. Polynucleotide arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon reading the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated by depositing previously obtained biopolymers (such as from synthesis or natural sources) onto a substrate, or by in situ synthesis methods. Methods of depositing obtained biopolymers include loading then touching a pin or capillary to a surface, such as described in U.S. Pat. No. 5,807,522 or deposition by firing from a pulse jet such as an inkjet head, such as described in PCT publications WO 95/25116 and WO 98/41531, and elsewhere. Such a deposition method can be regarded as forming each feature by one cycle of attachment (that is, there is only one cycle at each feature during which the previously obtained biopolymer is attached to the substrate). For in situ fabrication methods, multiple different reagent droplets are deposited by pulse jet or other means at a given target location in order to form the final feature (hence a probe of the feature is synthesized on the array substrate). The in situ fabrication methods include those described in U.S. Pat. No. 5,449,754 for synthesizing peptide arrays, and in U.S. Pat. No. 6,180,351 and WO 98/41531 and the references cited therein for polynucleotides, and may also use pulse jets for depositing reagents. The in situ method for fabricating a polynucleotide array typically follows, at each of the multiple different addresses at which features are to be formed, the same conventional iterative sequence used in forming polynucleotides from nucleoside reagents on a support by means of known chemistry. This iterative sequence can be considered as multiple ones of the following attachment cycle at each feature to be formed: (a) coupling an activated selected nucleoside (a monomeric unit) through a phosphite linkage to a functionalized support in the first iteration, or a nucleoside bound to the substrate (i.e. the nucleoside-modified substrate) in subsequent iterations; (b) optionally, blocking unreacted hydroxyl groups on the substrate bound nucleoside (sometimes referenced as "capping"); (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The coupling can be performed by depositing drops of an activator and phosphoramidite at the specific desired feature locations for the array. A final deprotection step is provided in which nitrogenous bases and phosphate group are simultaneously deprotected by treatment with ammonium hydroxide and/or methylamine under known conditions. Capping, oxidation and deprotection can be accomplished by treating the entire substrate ("flooding") with a layer of the appropriate reagent. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in another flooding procedure in a known manner. Conventionally, a single pulse jet or other dispenser is assigned to deposit a single monomeric unit.

The foregoing chemistry of the synthesis of polynucleotides is described in detail, for example, in Caruthers, Science 230: 281–285, 1985; Itakura et al., Ann. Rev. Biochem. 53: 323–356; Hunkapillar et al., Nature 310: 105–110, 1984; and in "Synthesis of Oligonucleotide Derivatives in Design and Targeted Reaction of Oligonucleotide Derivatives", CRC Press, Boca Raton, Fla., pages 100 et seq., U.S. Pat. Nos. 4,458,066, 4,500,707, 5,153,319, 5,869,643, EP 0294196, and elsewhere. The phosphoramidite and phosphite triester approaches are most broadly used, but other approaches include the phosphodiester approach, the phosphotriester approach and the H-phosphonate approach. The substrates are typically functionalized to bond to the first deposited monomer. Suitable techniques for functionalizing substrates with such linking moieties are described, for example, in Southern, E. M., Maskos, U. and Elder, J. K., Genomics, 13, 1007–1017, 1992. In the case of array fabrication, different monomers and activator may be deposited at different addresses on the substrate during any one cycle so that the different features of the completed array will have different desired biopolymer sequences. One or more intermediate further steps may be required in each cycle, such as the conventional oxidation, capping and washing steps in the case of in situ fabrication of polynucleotide arrays (again, these steps may be performed in flooding procedure).

Further details of fabricating biopolymer arrays by depositing either previously obtained biopolymers or by the in situ method are disclosed in U.S. Pat. Nos. 6,242,266, 6,232,072, 6,180,351, and 6,171,797. In fabricating arrays by depositing previously obtained biopolymers or by the in situ method, typically each region on the substrate surface on which an array will be or has been formed ("array regions") is completely exposed to one or more reagents. For example, in either method the array regions will often be exposed to one or more reagents to form a suitable layer on the surface which binds to both the substrate and biopolymer or biomonomer. In in situ fabrication the array regions will also typically be exposed to the oxidizing, deblocking, and optional capping reagents. Similarly, particularly in fabrication by depositing previously obtained biopolymers, it may be desirable to expose the array regions to a suitable blocking reagent to block locations on the surface at which there are no features from non-specifically binding to target.

In array fabrication, the quantities of polynucleotide available are usually very small and expensive. Additionally, sample quantities available for testing are usually also very small and it is therefore desirable to simultaneously test the same sample against a large number of different probes on an array. These conditions require use of arrays with large numbers of very small, closely spaced features. About 2 to 200 of such arrays can be fabricated on a rigid substrate (such as glass). Such a substrate must be manually or machine placed into a fabricating tool, and is later cut into substrate segments each of which may carry one or several arrays. To produce many more arrays requires placing and aligning of individual substrates in the fabricator. Furthermore, precisely cutting a substrate such as glass after the expensive arrays have been fabricated on it leads to some loss due to breakage. The substrate segments that are successfully cut are typically placed in individually in some apparatus for exposure to samples, again requiring repeated handling to expose many samples to respective arrays.

It would be desirable to provide a means by which many arrays can be conveniently fabricated on a substrate and prepared for use, which could reduce the need for handling and which would allow for ready exposure of the substrate to required reagents.

SUMMARY OF THE INVENTION

The present invention then, provides in one aspect, a method of forming one or more arrays of polymers each having a pattern of features on a surface of a flexible elongated web. The method may include applying the polymers or their precursor units to the surface at an application station (for example, a drop deposition station which deposits drops containing the polymers or precursors). The web is contacted with a reagent (for example, as by covering with a continuous volume of reagent) at a reagent station (for example, a reagent bath) which reagent chemically reacts with the polymers, precursors, or the web. The web is driven in a lengthwise direction through the application station and optionally also through the reagent station (and may even be driven in different directions between an input side of the application station and an output side of the reagent station). Any of the foregoing are repeated as needed to the form the one or more arrays along the web. Optionally, before or after any application or reagent station, the web is also driven through a wash station at which the web is exposed to a wash fluid (for example, a wash bath at which multiple features are covered with a continuous volume of wash fluid).

Many configurations of application, reagent, and wash stations (when present) are possible. For example, the web may repeatedly be driven through a same or different reagent stations such that the contacting of features with reagent is repeated on each of multiple surface regions of the web. At least some of the repetitions of the polymer or precursor application may occur simultaneously on different array regions at respective different application stations. There may be one or more of any of the application, reagent, or wash stations in various configurations. In one configuration, the web is driven in a continuous loop through a same application station and a same reagent station. In another configurations the web may be driven through one or more reagent stations (and optionally also one or more wash stations) before, after, or between application stations or, in still another configuration may be driven through multiple application stations without an intervening reagent station and then through one or more reagent stations (and optionally also one or more wash stations). The web may be driven in different directions at any time in its path of travel (for example, the web may be driven in different directions between at least two of the reagent stations).

When precursor units are applied at the application station, at each feature a unit deposited in one cycle becomes linked with a unit deposited in a subsequent cycle. A suitable reagent in such a case may, for example, be an oxidizing agent, or a deprotecting agent which deprotects a protected linking group of a unit deposited in a same cycle so that a unit deposited in a next cycle can link with the deprotected unit deposited in the preceding cycle. In one case where a polynucleotide array is to be fabricated using conventional phosphoramidite chemistry, the drop deposition station deposits drops containing nucleoside phosphoramidites, and the reagent includes at least one of a deprotecting reagent for deprotecting protected phosphoramidites or an oxidation reagent which oxidizes internucleoside phosphite bonds to phosphate bonds.

The present invention further provides a method of preparing a surface of an elongated web to receive a biopolymer array. The web is driven in a lengthwise direction from a supply reel and successively through one or more multiple surface treatment stations so as to provide a linking layer bound to the surface of less than 10 angstroms thickness (or less than 8, 6, or 4 angstroms thick) which layer has a polynucleotide, protein, nucleoside or amino acid minimum binding affinity of $10^4$ to $10^6$ units/$\mu^2$.

"Binding affinity" for a nucleoside, nucleic acid, protein, or amino acid can be determined as specified below (each reaction time of 10 seconds and all reactions at a temperature of 20° C.):

Nucleoside: Use spot activated T phosphoramidite. Deblock Trityl and collect the acid solution. Measure with UV the intensity of the signal at 498 nm. From that calculate the concentration and finally the number of molecules. This number divided by the surface area will give the binging affinity.

Nucleic Acid:DNA: Take Cy3 conjugated nucleic acid of the following sequence:

5'-GGA TAC ACT GAC CAG CTA CGA TGA T-3'

Deposit one drop on the surface. Measure intensity of fluorescence. From the intensity the number of molecule can be extracted. This number divided by the surface area will give the binging affinity.

Protein: Deposit a series of albumin spots with various dilution of a known concentration of the protein. Let it dry. Then add over each spot a small drop of buffer with a fluorescein-NHS ester. The intensity of fluorescein is measured. This gives a titration curve of the rate of conjugaison of the dye to the protein. Then spot the protein and wash. Add the fluorescein-NHS ester. After washing, the intensity of fluorescence is measured and compare to the titration curve. From it the total number of protein attached to the surface, or available, is deducted. This number divided by the surface area will give the binging affinity.

Amino Acid: Using Lysine, deprotect the side chain amine and react a Fluorescein—NHS ester on the amine. Quantify the fluorescence, get the amount of fluorescein, divide this number by the surface area to get the binding affinity.

Suitable linking layers may include, particularly for polynculeotide binding, any one or more of: polylysine; primary, secondary, tertiary or quaternary amines; avidin; or biotin. In the case where the linking layer is to link a protein it may, for example, be selected from any one or more of: antibodies against a part of the protein, or the recombinant protein (for example, protein A or G recombinant); a phosphorothioate; ahydrophobic surface such as phenyl; protein A or G attached to the surface; avidin; or biotin. Alternatively, such linking layers may include, particularly for nucleoside monomers (such as nucleoside phosphoramidites) any one or more of a: silane (such as a silane with a free amino group, or a mixture of different silanes); aldehyde; thiol, activated ester; diene; or pentadiene (precursor of ferrocene). Layer thickness can be evaluated using UV or X-ray elipsometry.

In any configuration of the present invention, the web may be directed in a path by one or more guides (such as rotatable guides) each contacting a web surface (such as the surface carrying the arrays) along opposite edge margins while not contacting a central portion of the web intermediate the edge margins. Such guides may be driven in order to drive the web, or may be idle (that is, not driven and they rotate in response to the web passing over them).

The present invention also provides for driving the web through a drop deposition station, with the web being restrained against one surface on either side of the drop deposition station and against the other surface on one or both sides of the drop deposition station so as to assist in maintaining the web flat while in the drop deposition station. In an alternative embodiment the web is supported at a surface position opposite a location on which drops are deposited on the surface to form the one or more arrays. Such support may be provided by a guide as described above.

The present invention further provides an apparatus which may execute any one or more methods of the present invention. One such apparatus includes the one or more application, reagent, and optional wash stations, in any configuration as described herein. Restraints and supports may be provided. A web tensioner may also be provided to assist in maintaining a constant tension of the web while in an application station. An optional web tension gauge measures web tension while in an application station. The present invention further provides a computer program product comprising a computer readable storage medium having a computer program stored thereon, for use with any suitable apparatus (such as any of the foregoing types), which program when loaded into a processor causes the apparatus to execute any one or more methods of the present invention.

The various aspects of the present invention can provide any one or more of the following and/or other useful benefits. For example, a large number of arrays can be fabricated on a single substrate (the web) before a substrate change is needed, the web can be inhibited from moving toward and away from a drop deposition apparatus during web fabrication, and the web can be readily exposed to required reagents.

BRIEF DESCRIPTION OF THE DRAWINGS

To facilitate understanding, the same reference numerals have been used, where practical, to designate the same elements that are common to the figures. Drawings are not necessarily to scale unless otherwise indicated

DETAILED DESCRIPTION OF EMBODIMENTS OF THE INVENTION

Figure 1:
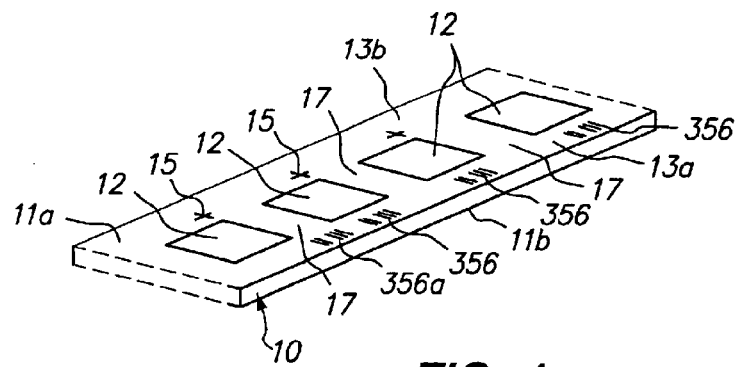
FIG. 1 illustrates an array assembly in the form of a web carrying multiple arrays, such as may be fabricated by methods of the present invention.

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948, 902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

A "drop" is a small amount of liquid traveling in a space, and while often approximately spherical if no external forces are acting upon it, may have other shapes depending upon those other forces. In the present case, a drop which has contacted a substrate is often referred to as a deposited drop, although sometimes it will be simply referenced as a drop when it is understood that it was previously deposited. Detecting a drop "at" a location, includes the drop being detected while it is traveling between a dispenser and that location, or after it has contacted that location (and hence may no longer retain its original shape) such as capturing an image of a drop on the substrate after it has assumed an approximately circular shape of a deposited drop. A "pulse jet" is a device which can dispense drops in the formation of an array. Pulse jets operate by delivering a pulse of pressure (such as by a piezoelectric or thermoelectric element) to liquid adjacent an outlet or orifice such that a drop will be dispensed therefrom.

A "set" of anything (such as a set of drops), may contain only one, or only two, or three, or any number of multiple drops (although where "drops" are referenced in relation to a set implies the set in that case includes multiple drops). A "group" of drops has multiple drops. An "array", unless a contrary intention appears, includes any one or two dimensional arrangement of addressable regions bearing a particular chemical moiety or moieties (for example, biopolymers such as polynucleotide sequences) associated with that region. Each region may extend into a third dimension in the case where the substrate is porous while not having any substantial third dimension measurement (thickness) in the case where the substrate is non-porous. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). An array feature is generally homogenous and the features typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" or "array characteristics", refers to one or more physical, chemical or biological characteristics of the array, such as feature positioning, one or more feature dimensions, or some indication of an identity or function (for example, chemical or biological) of a moiety at a given location, or how the array should be handled (for example, conditions under which the array is exposed to a sample, or array reading specifications or controls following sample exposure). "Hybridizing" and "binding", with respect to polynucleotides, are used interchangeably. During a "cycle" for forming a given feature, often at least 50% (and more typically at least 70%, 80% or more preferably at least 90% or 95%) of moieties bound to a substrate surface at a region at which precursor units or previously obtained complete moiety are exposed, and which are available to link with a deposited monomeric unit or previously obtained complete moiety for forming the desired feature, will actually link to such deposited monomeric unit or complete moiety.

A "plastic" is any synthetic organic polymer of high molecular weight (for example at least 1,000 grams/mole, or even at least 10,000 or 100,000 grams/mole.

"Flexible" with reference to a web references that the web can be bent 180 degrees around a roller of less than 1.25 cm in radius. The web can be so bent and straightened repeatedly in either direction at least 100 times without failure (for example, cracking) or plastic deformation. This bending must be within the elastic limits of the material. The foregoing test for flexibility is performed at a temperature of 20° C.

A "reagent station" (such as a "reagent bath") may expose use any fluid reagent, either liquid or gas (including plasma). A "wash station" (such as a "wash bath" on the other hand, uses a liquid to accomplish the washing. A "bath" structure can be any suitable design for holding the fluid or liquid, as the case may be.

"Hybridizing conditions" for a polynucleotide array refer to suitable conditions of time, temperature and the like, such that a target sequence present in solution will bind to an array feature carrying a complementary sequence to a greater extent than to features carrying only sequences which are not complementary to the target sequence (and preferably at least 20% or 100%, or even 200 or 500% greater).

A "web" references a long continuous piece of substrate material having a length greater than a width. For example, the web length to width ratio may be at least 5/1, 10/1, 50/1, 100/1, 200/1, or 500/1, or even at least 1000/1.

"Reference unit" in relation to fluorescence measurements herein means the maximum fluorescence obtainable from a fused silica, or one-third the maximum value obtainable from a borosilicate glass. All fluorescence measurements herein, unless otherwise indicated, are integrated fluorescence emission energies from 547 nm to 597 nm, which result from a 1 mm thick section of material, using a monochromated high pressure Xe lamp excitation source centered at 532 nm with a width at half-maximum of about 5 nm. All ratios assume the same unit area of illuminated material. The following may be used as the foregoing referenced materials (available from the National Institute of Standards and Technology, Maryland, U.S.A.): fused silica—Standard Sample 198; borosilicate glass-Standard Reference Material 93a.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top", "upper", and "lower" are used in a relative sense only. "Fluid" is used herein to reference a liquid. Reference to a singular item, includes the possibility that there are plural of the same items present. "May" refers to optionally. The steps of any method may be performed in the recited order, or in any other order that is logically possible. All patents and other references cited in this application, are incorporated into this application by reference except insofar as where any definitions in those references conflict with those of the present application (in which case the definitions of the present application are to prevail).

Figure 2:
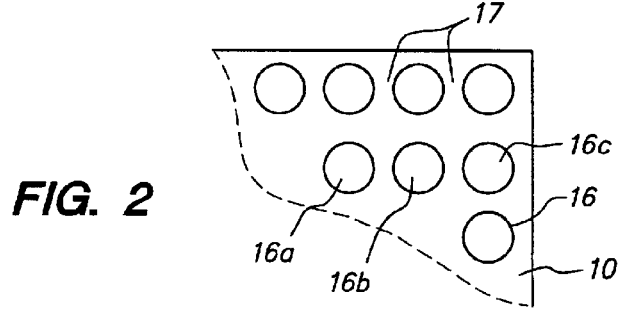
FIG. 2 is an enlarged view of a portion of FIG. 1 showing multiple ideal spots or features.
Figure 3:
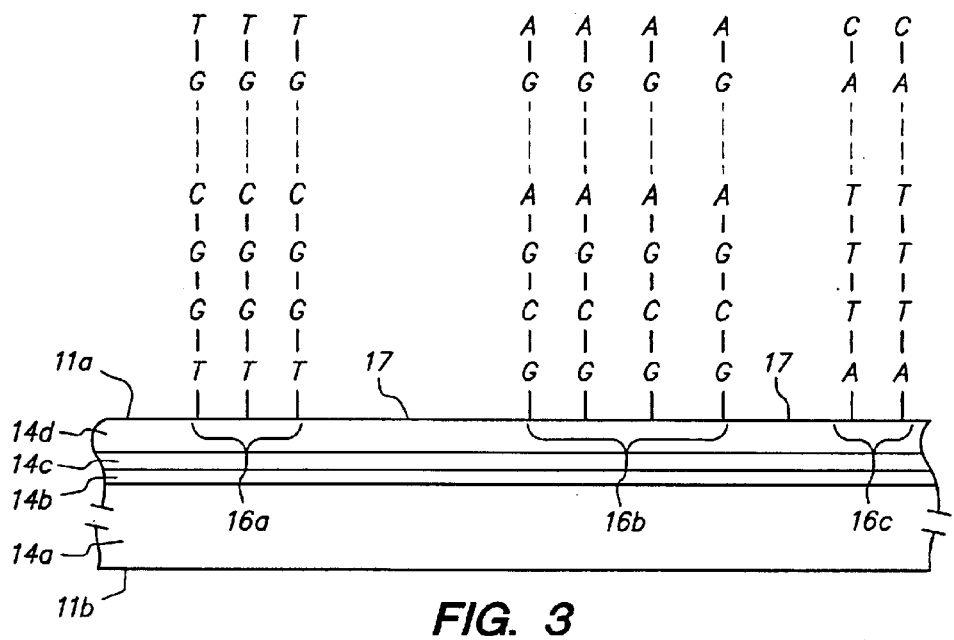
FIG. 3 is an enlarged illustration of a portion of FIG. 2.

Referring first to FIGS. 1–3, typically methods and apparatus of the present invention generate or use an array assembly which includes a substrate in the form of an elongated flexible web (or ribbon) 10 carrying one or more arrays 12 disposed along a front surface 11a of web 10 and separated by inter-array areas 17. A back side 11b of web 10 does not carry any arrays 12. The arrays on web 10 can be designed for testing against any type of sample, whether: a trial sample; reference sample, a combination of the foregoing; or a known mixture of polynucleotides, proteins, polysaccharides and the like (in which case the arrays may be composed of features carrying unknown sequences to be evaluated). While only four arrays 12 are shown in FIG. 1, it will be understood that web 10 and the embodiments to be used with it, may use any number of desired arrays 12 such as at least five, ten, twenty, fifty, or one hundred (or even at least five hundred, one thousand, or at least three thousand). The foregoing numbers of arrays will typically be arranged end to end along the lengthwise direction of web 10. To accommodate arrays 12, web 10 may be at least 100 cm (or at least 200 or 500 cm) in length, or may even be greater than 1 m (or greater than 2, 5 or 10 or 100 m) in length, with a width, for example, of less than 100 cm, or even less than 50, 30, 10, 5 or 1 cm. While only one array is positioned across the width of web 10, it is possible there could be more(for example two or three). Typically then, the ratio of the number of arrays 12 positioned lengthwise along web 10 to the number across the width may be at least 10/1, 20/1, 50/1, 100/1, or even at least 500/1 or at least 1000/1. Depending upon intended use, any or all of arrays 12 may be the same or different from one another and each will contain multiple spots or features 16 of biopolymers in the form of polynucleotides. A typical array may contain from more than ten, more than one hundred, more than one thousand or ten thousand features, or even more than from one hundred thousand features. All of the features 16 may be different, or some or all could be the same. In the case where arrays 12 are formed by the conventional in situ or deposition of previously obtained moieties, as described above, by depositing for each feature a droplet of reagent in each cycle such as by using a pulse jet such as an inkjet type head, interfeature areas 17 will typically (but not essentially) be present which do not carry any polynucleotide. It will be appreciated though, that the interfeature areas 17 could be of various sizes and configurations. It will also be appreciated that there need not be any space separating arrays 12 from one another. Each feature carries a predetermined polynucleotide (which includes the possibility of mixtures of polynucleotides). As per usual, A, C, G, T represent the usual nucleotides. It will be understood that there is usually a linker molecule (not shown) of any known types between the front surface 11a and the first nucleotide.

Web 10 also has opposite edge margins 13a, 13b along front surface 11a, along one edge margin 13a of which are provided identifiers in the form of bar codes 356. Identifiers such as other optical or magnetic identifiers could be used instead of bar codes 356 which will carry the information discussed below. Each identifier is positioned adjacent an associated array 12. However, this need not be the case and identifiers such as bar code 356a can be positioned elsewhere. Further, a single identifier might be provided which is associated with more than one array 12 and such one or more identifiers may be positioned on a leading or trailing end (neither shown) of web 10. Alignment fiducial marks 15 may also be present along edge margin 13b, each fiducial 15 associated with a corresponding adjacent array 12, for the purposes discussed below. Alternatively, bar codes 356 can be positioned along one or both of the edge margins 13a, 13b on back surface 11b. This can be advantageous since, as discussed below, back surface 11b may be of a plastic base layer onto which markings might be more easily provided (by printing or laser ablation) than onto front surface 11a. Web 10 may, for example, be at least 100 cm in length, or even at least 0.5 m or at least 1, 2, 5 or 10 m in length, with a width of at least 3 mm or even at least 5 mm, or 1, 2, 5 or 10 cm.

FIGS. 2 and 3 illustrate ideal features 16 of an array 12 where the actual features formed are the same as the target (or "aim") features, with each feature 16 being uniform in shape, size and composition, and the features being regularly spaced. Such an array when fabricated by drop deposition methods, would require all reagent droplets for each feature to be uniform in shape and accurately deposited at the target feature location. In practice, such an ideal result is difficult to obtain due to fixed and random errors during fabrication.

It will be seen from FIG. 3 that web 10 may have a number of different layers. A base layer 14a forms the greatest thickness and may consist of any flexible plastic such as a polyolefin film (such as polypropylene, polyethylene, polymethylpentene) or polyetheretherketone, polyimide, any of the flurocarbon polymers or other suitable flexible thermoplastic polymer film. The material of base layer 14a is best selected to provide stable dimensional, mechanical, and chemical properties under the conditions web 10 will be used. For example, for polynucleotide arrays web 10 will be subject to elevated temperatures (for example, 60°) for long times (for example, 12 hours) in aqueous environments. Polyester or aramid films exposed to such conditions may tend to swell or degrade. When the type of arrays 12 and the conditions to which the layer 14a will be exposed, are selected, base layer 14a can be selected for dimensional, mechanical and chemical stability under such conditions by reference to many known polymer film characteristic sources such as: "New Characterization Techniques for Thin Polymer Films", Ho-Ming Tong (Editor), Luu T. Nguyen (Editor), ISBN: 0-471-62346-6; "Polymer Surfaces and Interfaces II", W. J. Feast (Editor), H. S. Munro (Editor), R. W. Richards (Editor), ISBN: 0-471-93456-9; "Functional Organic and Polymeric Materials: Molecular Functionality—Macroscopic Reality", Tim H. Richardson (Editor), ISBN: 0-471-98724-7; the polymer property searchable database "Polymers—A Property Database", Ellis, Bryan Sheffield University, UK, ISBN/ISSN: 0849310555; "Handbook of Plastic Materials and Technology", (Irvin, I Rubin, ed); "Modern Plastics Encyclopedia"; "Plastics Design Library Chemical Resistance"; the guide available at the world wide web site address of boedeker.com/mguide.htm which is Boedeker Material Selection Guide for plastics; or the world wide web site address at Knovel.com which also offers an on-line polymers properties database. Base layer 14a will typically have a thickness of more than 1 $\mu$m (or more than 5 $\mu$m) and less than 500 $\mu$m (or even less than 100, 50, 25, or 15 $\mu$m).

Web 10 also includes an optional reflective layer 14c and a transparent layer in the form of glass layer 14d. Reflective layer 14c may be aluminum, silver, gold, platinum, chrome or other suitable metal film deposited by vacuum deposition, plasma enhanced chemical vapor deposition or other means onto base layer 14c or an optional intermediate bonding layer 14b. Alternatively, the reflective layer may be constructed using multiple dielectric layers designed as a dielectric Bragg reflector or the like. Typically, such a reflector is constructed by repeating ¼ wave thick layers of two optically clear dielectric which have differing indices of refraction. Design considerations for such a reflector include the excitation and emission wavelengths and the angle of incidence for the excitation beam and detector. Rigid multi-layer dielectric reflectors are well known in the industry and can be purchased from Oriel Instruments, Connecticut, U.S.A. Bonding layer 14b, if used, may be any suitable material which is flexible at the thickness used and bonds to both base layer 14a and reflective layer 14c. Reflectively coated plastic films are well known and commercially available. Glass layer 14d (which term is used to include silica) may be deposited onto reflective layer 14c by sputtering, plasma enhanced chemical vapor deposition or similar techniques such as described in. Glass layer 14d may optionally be used without reflective layer 14c. Several manufacturers have commercial capabilities for providing films coated with metal and glass layers, for example, Sheldahl Corporation, Northfield, Minn. (see the world wide web site at sheldahl.com), and General Atomic, San Diego, Calif. (world wide web site address of ga.com) Glass layer 14d may have any suitable thickness, for example greater than 1, 10 or 100 nm, and less than 1000, 700, or 400 nm but typically has a thickness about ¼ wavelength of the light used to illuminate array features during reading, or an odd multiple of that amount. For example, 40 to 200 nm, or 60 to 120 nm (or even 80 to 100 nm), or an odd integer multiple of any of the foregoing thickness ranges (for example, 300 nm may be used) provided the layer is not so thick that web 10 is no longer flexible.

Reflective layer 14c, and bonding layer 14b may each have a thickness of less than 50 nm, or even less than 20, 10, 5 or 1 nm (but in any case, for example, more than 0.1 or 0.5 nm). In one example, bonding layer 14b may be 10 nm. Reflective layer 14c may particularly be chosen to have a thickness such that it is opaque to the wavelength of the light used for illuminating the features during array reading. Glass layer 14d may particularly have a thickness and transparency selected as described in U.S. patent application Ser. No. 09/493,958 titled "Multi-Featured Arrays With Reflective Coating" filed Jan. 28, 2000 by Andreas Dorsel et al, while reflective layer 14c may meet the reflectivity requirements in relation to the illuminating light as mentioned in that application. For example, reflective layer 14c may reflect at least 10% of the incident light, or at least 20%, 50%, 80% or at least 90%, or even at lest 95%, of the incident light. As mentioned previously, this and the other references cited herein are incorporated into this application by reference. However, the glass layer 14d and reflective layer 14c may not meet those requirements.

In the above configuration of web 10, the use of a glass layer 14d allows the use of conventional chemistries for substrate coating, feature fabrication, and array usage (for example, hybridization in the case of polynucleotide arrays). Such chemistries are well known for arrays on glass substrates, as described in the references cited herein and elsewhere. Furthermore, using reflective layer 14c not only can provide the useful characteristics mentioned in the above referenced patent application Ser. No. 09/493,958, but can avoid undesirable optical characteristics of the plastic base layer 14a (for example, undesirable fluorescence, and in the case of a plastic web that absorbs the incident light energy, excessive heating and possible melting of the substrate). This allows for the ability to use base layers 14a of a material which may have a high fluorescence and/or high absorbance of incident light. For example, the plastic base layer 14a may have a fluorescence of at least five or ten (or even at least: twenty, fifty, one-hundred, or two-hundred) reference units, and/or an absorbance of the illuminating light used to read arrays 12 of at least 5%, 10%, 20%, or 50% (or even at least 70%, 90% or 95%).

Use of a non-reflective opaque layer (for example, a suitably dyed plastic or other layer) in place of reflective layer 14c also allows the use of the foregoing materials for base layer 14a although in such a case some heat may then be generated in the opaque layer. A reflective or non-reflective opaque layer at the position of layer 14c, may block at least 10% of the illuminating light incident on front surface 11a for reading arrays 12, and even at least 20%, 50%, or 80% (or at least 90% or 95%) of the illuminating light. A non-reflective opaque layer may reflect less than 95%, 90%, 80%, or 50% (or even less than 10%) of the illuminating light. Where neither a reflective layer 14c or other opaque layer is present, it will be preferable to employ a base layer 14a that emits low fluorescence upon illumination with the excitation light, at least in the situation where the array is read by detecting fluorescence. Base layer 14a in this case may emit less than two-hundred, one-hundred, fifty, or twenty (or even less than ten or five) reference units Additionally in this case, the base layer 14a is preferably relatively transparent to reduce the absorption of the incident illuminating laser light and subsequent heating if the focused laser beam travels too slowly over a region. For example, the base layer 14a may transmit at least 5%, 10%, 20%, or 50% (or even at least 70%, 90%, or 95%), of the illuminating light incident on front surface 11a. Note that all reflection and absorbance measurements herein, unless the contrary is indicated, are made with reference to the illuminating light incident on front surface 11a for reading arrays 12 and may be measured across the entire integrated spectrum of such illuminating light or alternatively at 532 nm or 633 nm.

Figure 4:
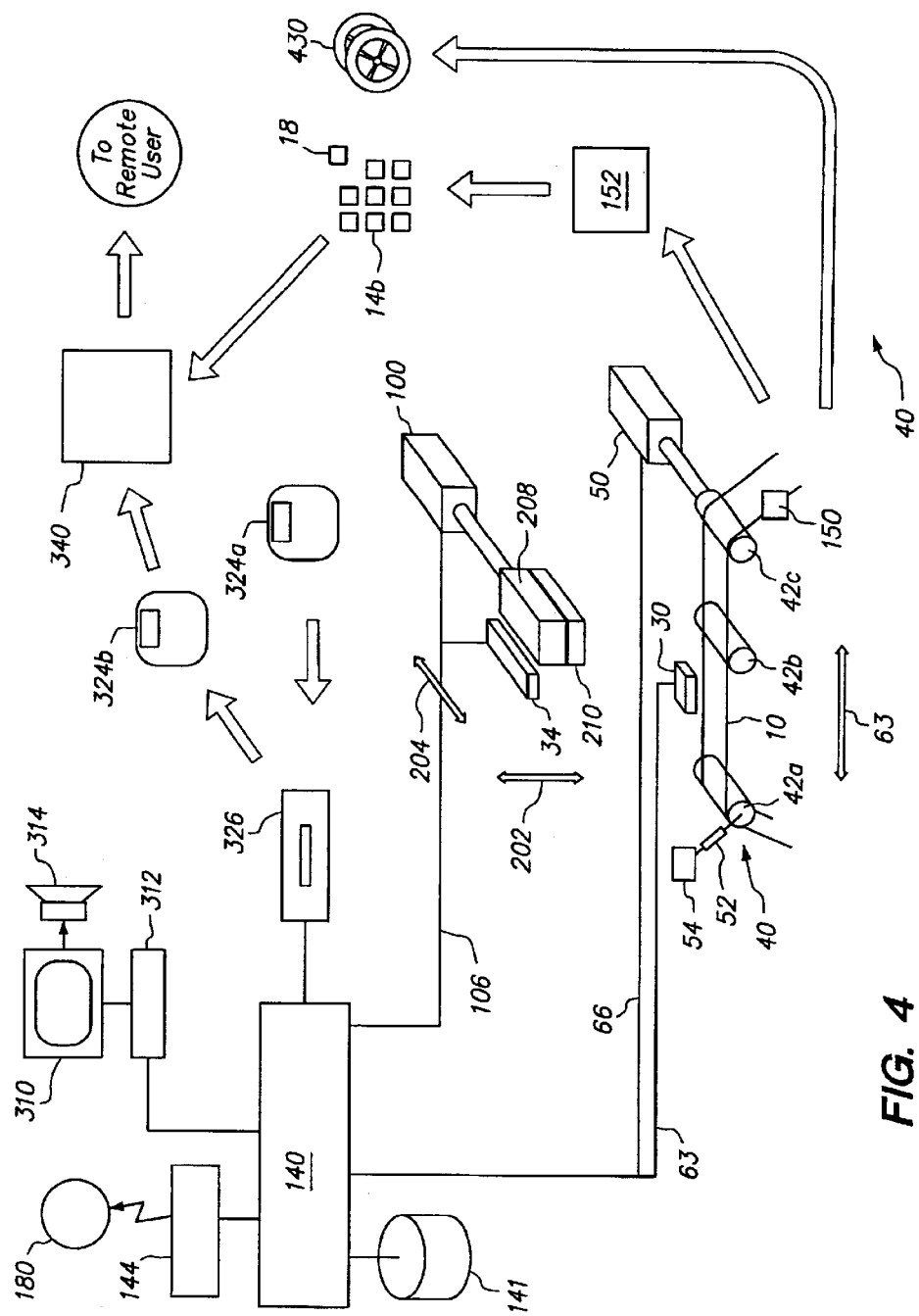
FIG. 4 schematically illustrates portions of an array fabricating apparatus of the present invention.
Figure 5:
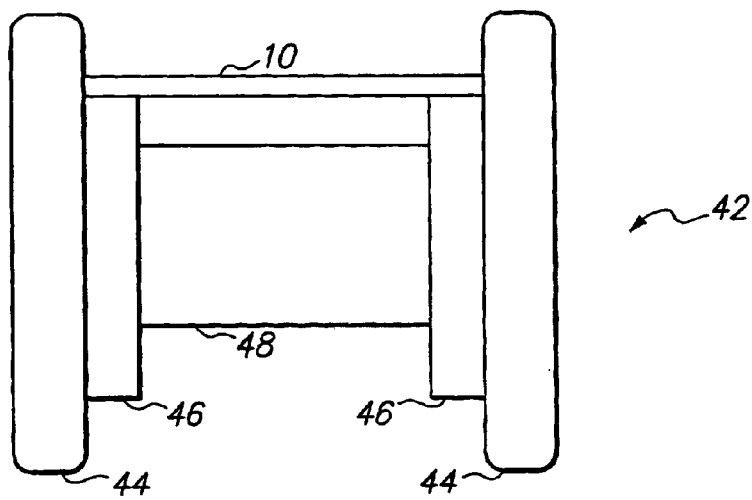
FIG. 5 is an enlarged view of a roller as may be used in any apparatus of the present invention.
Figure 6:
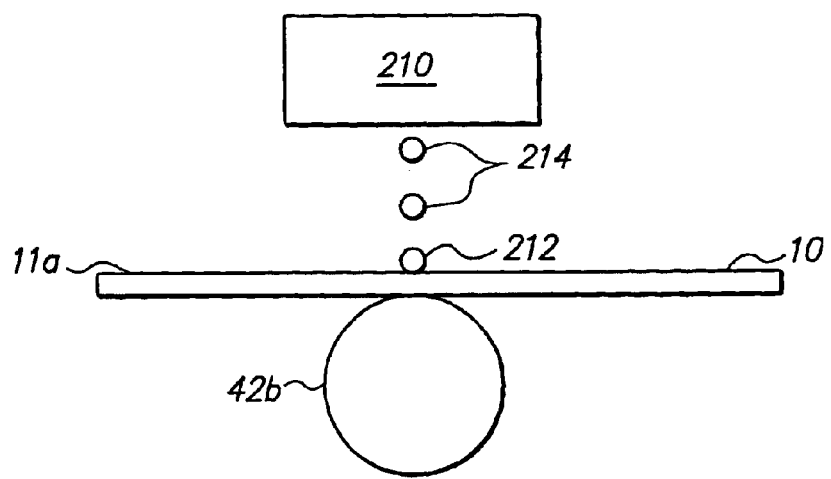
FIG. 6 is an enlarged view showing one possible arrangement in which drops are deposited on the web.

Referring now to FIG. 4, many of the components of an apparatus of the present invention which can execute a method of the present invention, will now be described. The apparatus of FIG. 4 represents most of the components of a fabrication station which includes an application station in the form of a drop dispensing head 210 which is retained by a head retainer 208. The positioning system includes a web transport system 40 which includes rotatable guides in the form of rollers 42a, 42b, 42c. A web tensioned in the form of an adjustable spring 52 is provided to maintain an constant tension on the web while beneath head 210. The value of the constant tension can be adjusted while web tension gauge 54 measures such tension value while web 10 is beneath head 210. At least one of the rollers 42c is driven by a reversible motor 50 of web transport system 40 so as to drive web 10 when engaged over rollers 42 in the direction of axis 63. Any roller 42 disclosed herein may be driven another motor (not shown) the same as motor 50 as may be required for sufficient traction to drive web 10 as required. At least each of rollers 42 in FIG. 4 or any of the other FIGS herein, which comes into contact with front surface 11a of web 10 may have the construction shown more clearly in FIG. 5. In this construction roller 42 has opposite ends 44, shoulders 46, and an intermediate section 48, with circular cross-sections of decreasing diameter moving from an end 44 to shoulder 46 to the intermediate section 48, as illustrated in FIG. 5. This allows shoulders 46 to contact a surface 11a or 11b of web 10 along opposite edge margins while not contacting a central portion of the web intermediate the edge margins (which, at least on front surface 11a, carries arrays 12). Thus, even if front surface 11a of web 10 should be facing toward intermediate section 48 (as may occur in some of the other FIGS), arrays 12 thereon will still not contact any surface of roller 42. Of course, central portion 48 could be omitted entirely with either roller end section (which consists of an end 44 and its adjacent shoulder 46) independently mounted for rotation. Those rollers 42 which only contact back side 11b of web 10 may be cylinders or may also have the construction shown in FIG. 5. However, roller 42b may in particular be a cylinder of circular cross-section such that web 10 is supported completely across its width at a location 212 (which may be a line) at which drops 214 are deposited on web 10 (that is, the surface of roller 42b contacts the back side 11b across the width of web 10 at a position immediately opposite location 212). Such support restrains web 10 from movement in a direction of axis 202 at least at location 212. In many of the FIGS. it will be seen that the direction of travel of web 10 changes as it passes over a roller 42, such direction changing by more than 10, 20, 30, or more than 45 degrees, sometimes changing by as much as 90 or 180 degrees, (that is, the web then travels in a direction opposite from which it originally came, as is the case for web 10 passing over rollers 42 positioned at the bottom of reagent or wash baths in the FIGS described below).

Returning to FIG. 4, motor 50 is controlled by processor 140 through line 66, while a transporter 100 of the positioning system is controlled by processor 140 through line 106. Motor 50 is used to execute one axis positioning of web 10 facing the dispensing head 210, by moving it in the direction of arrow 63, while transporter 100 is used to provide adjustment of the position of head retainer 208 (and hence head 210) in a direction of axis 204. In this manner, head 210 can be scanned line by line, by scanning along a line over web 10 in the direction of axis 204 using transporter 100, while line by line movement of web 10 in a direction of axis 63 is provided by motor 50. In the case of forming arrays 12 by depositing previously obtained biopolymers, a load station (not shown) may also be provided such that head 210 can be positioned over it for polynucleotides or other biopolymers obtained from different vessels to be loaded into head 210. Such a load station and method of use is described in detail in U.S. patent application Ser. No. 09/183,604 for "Method And Apparatus For Liquid Transfer" filed Oct. 30, 1998 by Tella et al, incorporated herein by reference. Alternatively, head 210 can communicate with reagent reservoirs (not shown) containing phosphoramidite and activator reagents suitable for fabricating polynucleotide sequences on web 10 using the known in situ process. Head 210 may also optionally be moved in a vertical direction 202, by another suitable transporter (not shown). It will be appreciated that other scanning configurations could be used.

It will be appreciated that instead of transporter 100 moving the head 210 on the axis 204, head 210 could remain stationary and web transport system 40 could instead be moved in the direction of axis 204. Thus, when the present application recites "positioning" one element (such as head 210) in relation to another element (such as one of the stations 20 or web 10) it will be understood that any required moving can be accomplished by moving either element or a combination of both of them. The head 210, the positioning system, and processor 140 together act as the deposition system of the apparatus. An encoder 30 communicates with processor 140 to provide data on the exact location of web 10 while encoder 34 provides data on the exact location of holder 208 (and hence head 210 if positioned correctly on holder 208). Any suitable encoder, such as an optical encoder, may be used which provides data on linear position. Encoder 30 provides web 10 location data by identifying the location of fiducials 15 on web 10 (see FIG. 1).

Processor 140 also has access through a communication module 144 to a communication channel 180 to communicate with a remote station. Communication channel 180 may, for example, be a Wide Area Network ("WAN"), telephone network, satellite network, or any other suitable communication channel. Communication module 144 may be any module suitable for the type of communication channel used, such as a computer network card, a computer fax card or machine, or a telephone or satellite modem. A reader 142 further communicates with processor 140.

Head 210 may have multiple pulse jets, such as piezoelectric or thermoelectric type pulse jets as may be commonly used in an ink jet type of printer and may, for example, include multiple chambers each communicating with a corresponding set of multiple drop dispensing orifices and multiple ejectors which are positioned in the chambers opposite respective orifices. Each ejector is in the form of an electrical resistor operating as a heating element under control of processor 140 (although piezoelectric elements could be used instead). Each orifice with its associated ejector and portion of the chamber, defines a corresponding pulse jet. It will be appreciated that head 210 could, for example, have more or less pulse jets as desired (for example, at least ten or at least one hundred pulse jets). Application of a single electric pulse to an ejector will cause a drop to be dispensed from a corresponding orifice. Certain elements of the head 210 can be adapted from parts of a commercially available thermal inkjet print head device available from Hewlett-Packard Co. as part no. HP51645A. A suitable head construction is described in U.S. patent application Ser. No. 09/150,507 filed Sep. 9, 1998 by Caren et al. for "Method And Multiple Reservoir Apparatus For Fabrication Of Biomolecular Arrays", incorporated herein by reference. Alternatively, multiple heads could be used instead of a single head 210, each being similar in construction to head 210 and being movable in unison by the same transporter or being provided with respective transporters under control of processor 140 for independent movement.

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

Of course, drop deposition devices other than pulse jets may be less desirably used. For example, contact drop deposition devices such as pins, open and closed capillaries and the like, may instead be used.

The apparatus can deposit drops to provide features which may have widths (that is, diameter, for a round spot) in the range from a minimum of about 10 $\mu$m to a maximum of about 1.0 cm. In embodiments where very small spot sizes or feature sizes are desired, material can be deposited according to the invention in small spots whose width is in the range about 1.0 μm to 1.0 mm, usually about 5.0 μm to 500 μm, and more usually about 10 μm to 200 μm. Non-round features may have area ranges equivalent to that of circular features with the foregoing width (diameter) ranges.

The apparatus further includes a display 310, speaker 314, and operator input device 312. Operator input device 312 may, for example, be a keyboard, mouse, or the like. Processor 140 has access to a memory 141, and controls print head 210 (specifically, the activation of the ejectors therein), operation of the positioning system, operation of each jet in print head 210, and operation of display 310 and speaker 314. Memory 141 may be any suitable device in which processor 140 can store and retrieve data, such as magnetic, optical, or solid state storage devices (including magnetic or optical disks or tape or RAM, or any other suitable device, either fixed or portable). Processor 140 may include a general purpose digital microprocessor suitably programmed from a computer readable medium carrying necessary program code, to execute all of the steps required for by the present invention for array production, or any hardware or software combination which will perform those or equivalent steps. The programming can be provided remotely to processor 141, or previously saved in a computer program product such as memory 141 or some other portable or fixed computer readable storage medium using any of those devices mentioned below in connection with memory 141. For example, a magnetic or optical disk 324a may carry the programming, and can be read by disk writer/reader 326.

A writing system which is under the control of processor 140, includes a writer in the form of a printer 150 which applies identifiers onto web 10 by printing them in the form of the bar codes 356 directly onto web 10 (or indirectly such as onto a label later attached to the substrate), each in association with a corresponding array 12 as illustrated in FIG. 1. In this context "printing" is used to include any appropriate means of applying the identifiers, such as by ink, laser ablation, impressing, and the like. Alternatively, the identifiers can by applied onto a housing carrying the substrate or label to be applied to such substrate or housing. Printer 150 may accomplish this task before or after formation of the array by the drop deposition system. Further, while printer 150 is shown located immediately after the deposition system in FIG. 4, it can be located at any suitable location within or after any of the configurations described in connection with FIGS. 7 to 11 below. In the case where printer 150 is located before the deposition system, it may also be used to print fiducial marks 15 as well as identifiers 356. Further, when the identifiers 356 are provided on web 10 before the deposition system they can be read by a reader (not shown) and information on array characteristics retrieved using them (for example, from the identifiers 356 themselves or from array layout information stored in memory 141 in association with respective identifiers). Such array layout information retrieved before deposition, can be used by processor 140 to control drop deposition so as to fabricate an array in accordance with one or more characteristics as specified by the array layout.

The identifiers may include an identifier which is generated and used as described in U.S. Pat. No. 6,180,351 titled "Chemical Array Fabrication with Identifier". The identifiers may also optionally include a communication address which identifies the address of a remote location on communication channel 180 from which one or more characteristics of an array will be communicated in response to a received communication of the associated identifier. Such remote location may be that of communication module 144 or alternatively that of another accessible memory on a communication channel carrying the database of array characteristic data and associated identifiers. Examples of a communication address may be a telephone number, computer ID on a WAN, or an internet Universal Resource Locator. The writing system further includes a data writer/reader 326 (such as an optical or magnetic disk drive) which can write data to a portable computer readable storage medium (such as an optical or magnetic disk). Optionally, a cutter 152 is provided to cut web 10 into array assemblies in the form of individual array units 18 each carrying a corresponding array 12 and bar code 356. Cutter 152 may be positioned at any suitable location after any of the configurations described in connection with FIGS. 8 to 11 below. Alternatively, web 10 with fabricated arrays 12 thereon may be wound onto a reel 430 (such as reels 430a or 430b described below).

Figure 7:
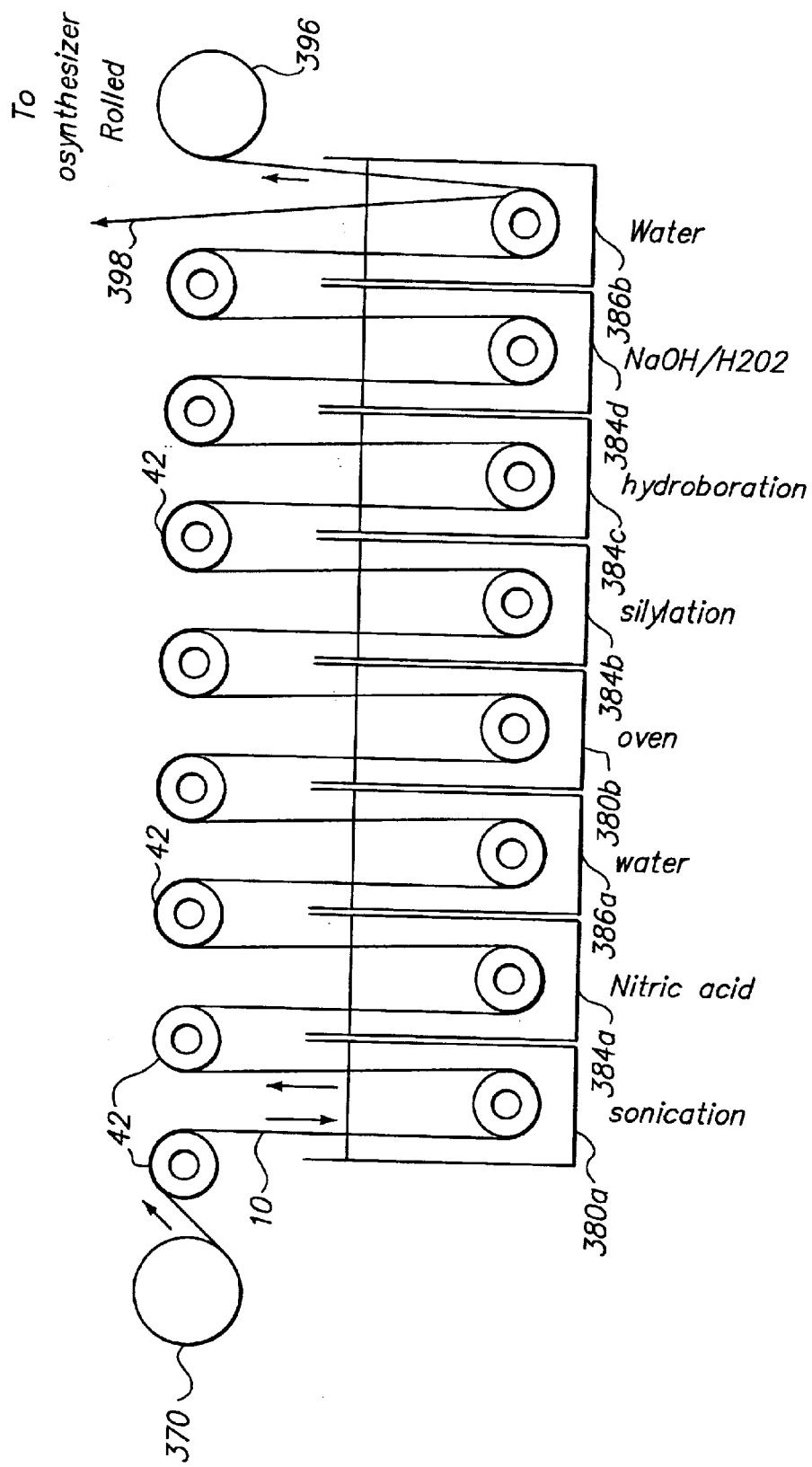
FIG. 7 illustrates an apparatus and method of the present invention for preparing a surface of a web for receiving an array to be formed thereon.

The above described components in FIG. 4 represent many of the components of an apparatus for producing an addressable array, which is sometimes referenced herein as a "fabrication station". Additional elements which may be part of a fabrication station are illustrated in various configurations in FIGS. 7–11. Referring first to FIG. 7 is shown a web surface treatment system provided to coat web 10 with a silane linking layer, which may use a single silane or a mixed silane layer, using a plurality of treatment stations. Such silane layers and the details of their formation are described, for example, in U.S. Pat. Nos. 6,235,488 and 6,258,454 and the references cited therein. Silane layers are particularly useful for forming arrays thereon using the in situ array fabrication method described above. The surface treatment system includes the following treatment stations: sonication station 380a, oven station 380b; reagent stations in the form of nitric acid bath 384a, silylation bath 384b, hydroboration bath 384c, and NaOH/$H_2O_2$ bath 384d; as well as rinse stations in the form of two water baths 386a, 386b. Details of the solutions and procedures can particularly be found in the foregoing U.S. Pat. No. 6,258,454. Sonication station 380a and the rinse stations provide for cleaning web 10, if needed, while oven station 380b provides for drying. It is noted that several of processes employed for applying the metal and/or glass layers onto the web are inherently clean processes, thus further cleaning may not be needed. The web 10 is provided from spool 370 and already includes the layers 14a through 14d already described, and is driven in a lengthwise direction through all of the foregoing stations in FIG. 7 by the web transport system as already discussed. After emerging from water bath 386b, the resulting web may either be wound on a spool 396 for later use or directed toward an application station as indicated by arrow 398. Arrow 398 in FIG. 9 shows an input of such a coated web 10 into multiple application and reagent stations for forming arrays by the in situ method as is discussed further below.

Note that at any reagent station 384 herein, multiple features 16 are simultaneously covered with a continuous volume of reagent (the liquid in the bath) which chemically reacts with polymer, polymer precursor units, or the web 10 itself (specifically, surface 11a thereof). Also, at any wash station 386 the continuous volume of wash liquid in the baths simultaneously covers multiple features. Similarly, multiple features 16 are simultaneously exposed to the conditions of any treatment station 380. The baths illustrated are all of the form of an upwardly open end container partly filled with the reagent or wash liquid. Note that the multiple features so simultaneously covered or exposed in any case, are on the same array but in addition multiple features on each of different arrays may be so simultaneously covered or exposed in any case.

Figure 8:
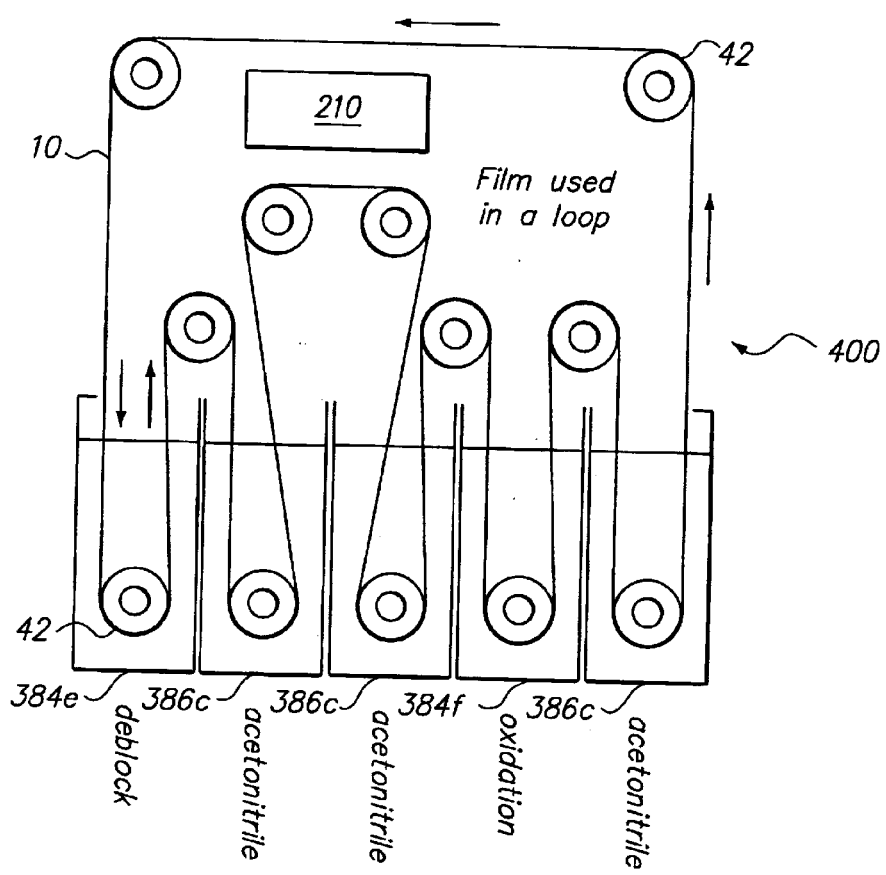
FIGS. 8 to 11 schematically illustrate various configurations of a method and apparatus of the present invention for fabricating arrays.

FIG. 8 illustrates one configuration of application and reagent stations which may be used for the in situ array fabrication method in the apparatus of FIG. 4, as described above. In particular web 10 is driven by the web transport system in a continuous loop in the direction of the arrows repeatedly through a same application station (head 210) and then through an acetonitrile wash bath 386c, oxidation reagent station 384f, another acetonitrile wash bath 386c, deblock reagent station 384e, and then further acetonitrile wash bath 386c, before returning to head 210. Head 210 in FIG. 8 is the head 210 shown in FIG. 4 (although in FIGS. 8 to 10 roller 42b has been omitted for simplicity). An oxidizing reagent at oxidation reagent station 384f oxidizes internucleoside pbosphite bonds to phosphate bonds, while a deprotection reagent deprotects nucleoside phosphoramidites, both in accordance with known in situ synthesis techniques mentioned above and in the cited references. Wash baths 386c and reagent stations 384e, 384f, are collectively referenced as a treatment block 400. An appropriate length of web 10 to form the continuous loop can be cut and spliced from spool 396 following surface treatment. Each time web 10 passes beneath head 210 an additional set of activated phosphoramidite drops may be deposited so that each time feature locations complete a cycle around the loop in the configuration of FIG. 8, another nucleotide has been added to a growing polynucleotide chain using the in situ array fabrication method already described. Thus, in the in situ array fabrication process where drops containing monomeric units of nucleoside phosphoramidites are deposited by head 210, the loop of web 10 in FIG. 8 will normally complete n cycles in the path of the loop, where n is the number of units in the longest chain to be formed at any feature 16.

Figure 9:
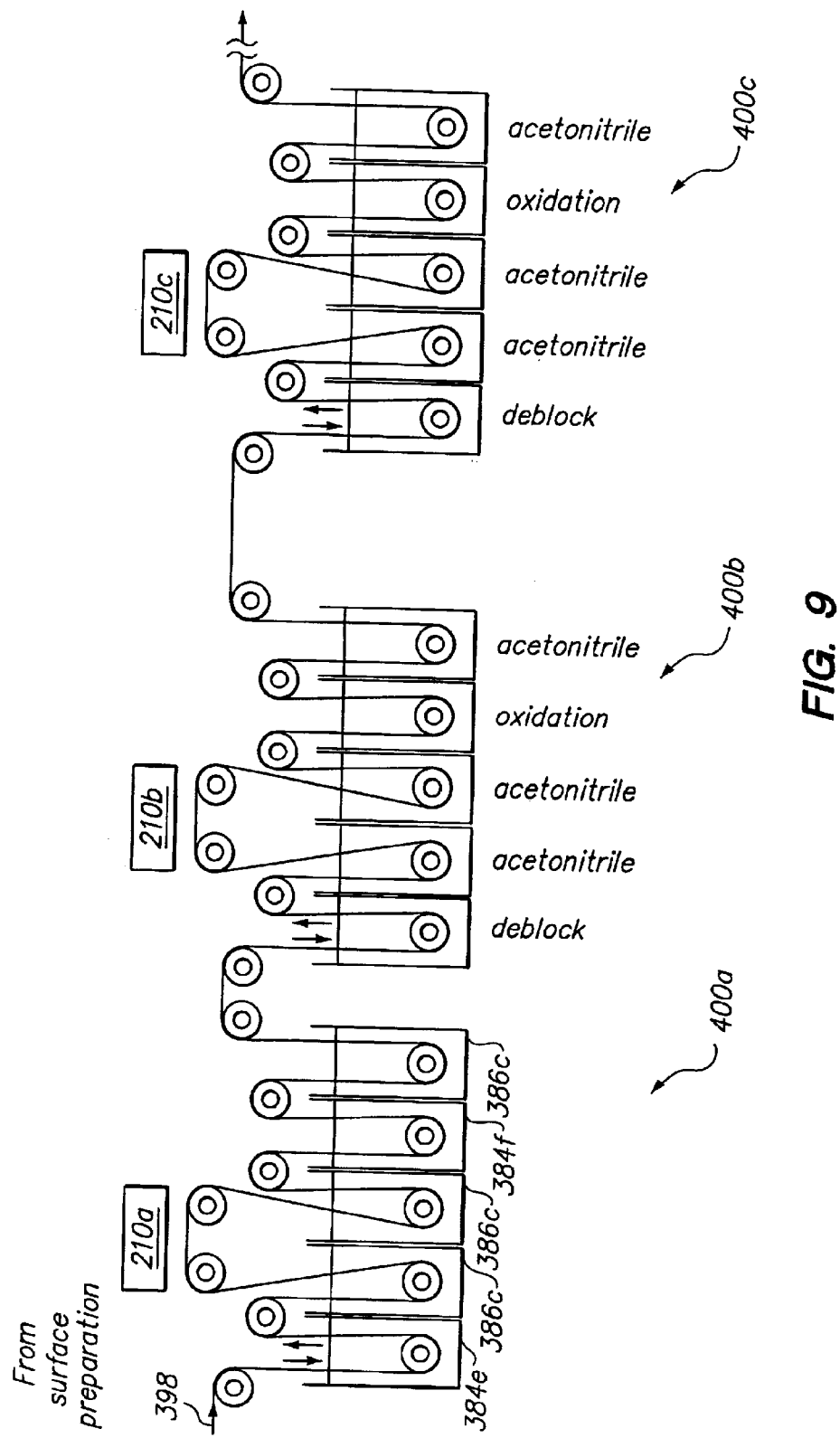
Figure 10:
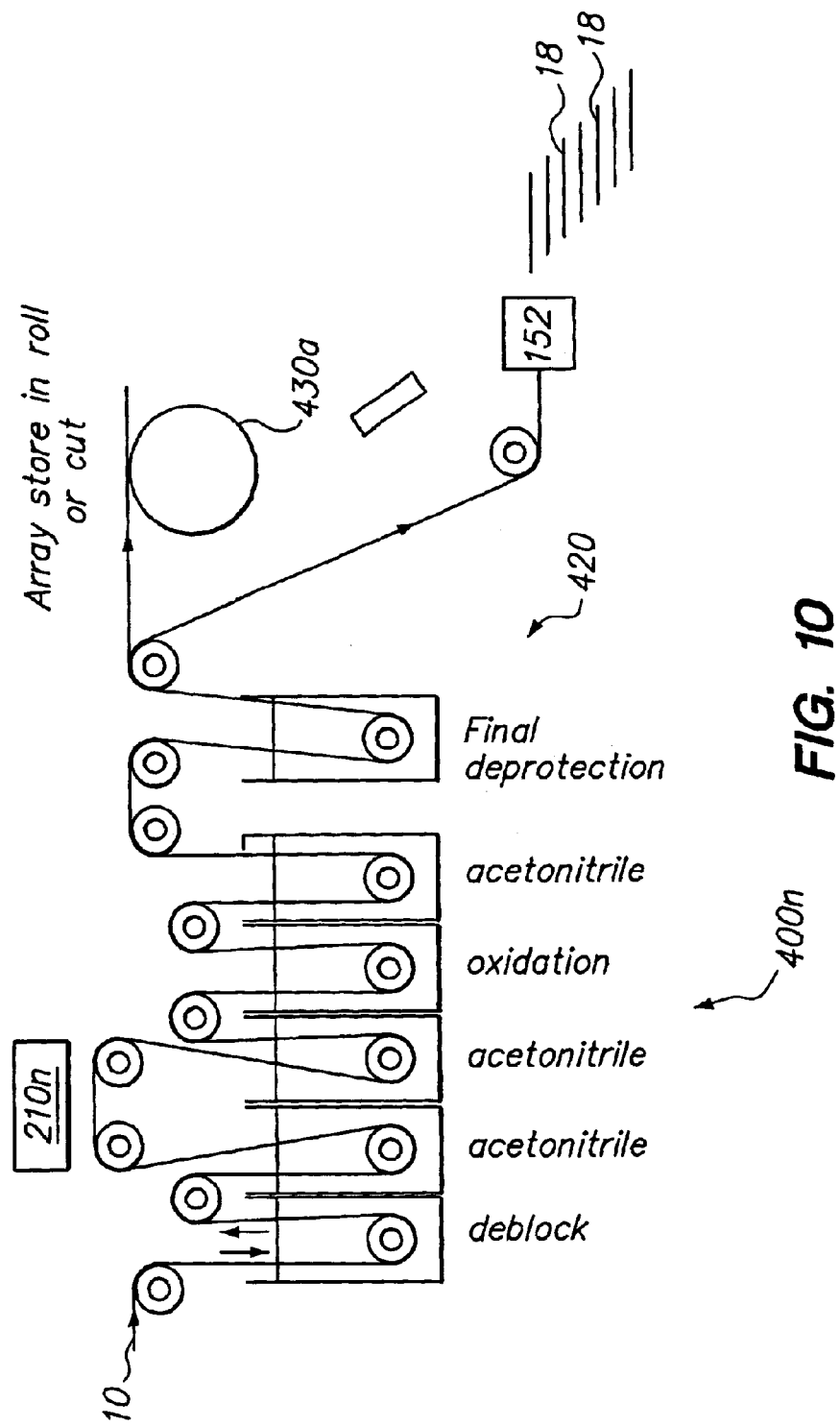

Referring now to FIG. 9, an alternate configuration to that of FIG. 8 is shown. In the configuration of FIG. 9 instead of driving a continuous loop of web 10 being driven through an application, reagent and wash stations multiple times (such as n times), it is instead driven in series through n different head 210 and treatment block 400 combinations with the output of one combination being input to the next until the final head 210 and treatment block 400 combination. That is, head 210a and treatment block 400 form one such combination, while head 210b and treatment block 210b form the next such combination, head 210c and treatment block 400c form the next, while head 210n and treatment block 400n in FIG. 10 form the final such combination. Thus, web 10 is driven sequentially through multiple reagent stations between different application stations with a new layer of nucleotides being formed at the different features 16 after each head 210 and treatment block 400 combination. For example, if all features 16 on web 10 (or the feature with the longest desired polynucleotide) are to be twenty-five units in length, then twenty-five head 210 and treatment block 400 combinations may be used. After exiting from head 210n and treatment block 400n, web 10 can then be driven through a final ammonium hydroxide and/or methylamine and/or ethanolamine deprotection reagent bath 420 of FIG. 10 under known in situ fabrication conditions. Web 10 may then be cut by cutter 152 or wound upon a reel 430a.

Each head 210 (which includes heads 210a to 210n) is independently operable by processor 140. That is, each head 210 is not mechanically connected to the other heads 210. Additionally each head 210 can be moved on axis 202 or 204 independently of the other heads 210, while the pulse jets of each head 210 can be operated by processor 140 independently of pulse jets on other of the heads. However, while heads 210 are operable independently, this does not exclude the possibility of processor 140 actually operating them in synchronization in fabrication of particular arrays 12.

Figure 11:
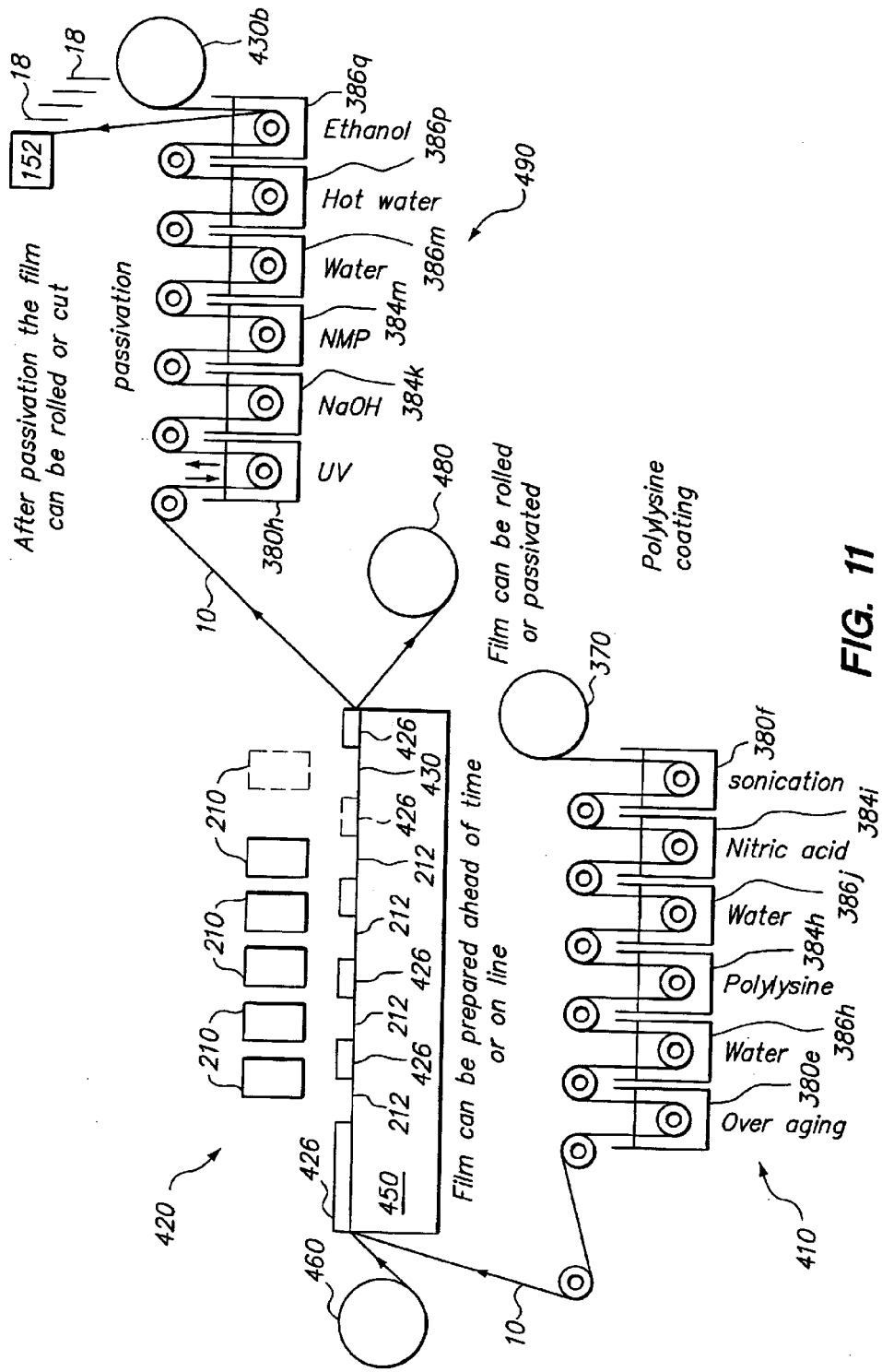

Turning now to FIG. 11, an alternate configuration which can replace those configurations of FIGS. 7 through 10 in the fabrication apparatus of FIG. 4, is illustrated. The configuration of FIG. 11 is used for the fabrication of arrays using the method of depositing previously obtained polynucleotides. Prior to use web 10 is provided with a surface treatment, such as a bound polylysine linking layer, suitable for receiving and binding such deposited polynucleotides. In particular, in FIG. 11 web 10 is driven from reel 370 in sequence through sonication treatment unit 380f, nitric acid reagent station 384i, water wash bath 386j, if necessary, all to clean web 10 (particularly surface 11a thereof), then through polylysine reagent station 384h to provide the polylysine coating (sometimes referenced as a "layer"), then water wash bath 386h, and an oven/aging treatment unit 380e. The oven portion of treatment unit 380c dries the web 10 while the aging treatment provides several hours of aging (for example, at least 2 or at least 4, 5, 8, or 12 hours). Regardless of whether a coating is provided for polynucleotides or for nucleoside monomers (as in FIG. 7), it will typically meet the thickness and binding affinity characteristics already mentioned above. To provide sufficient aging time unit 380e should be sufficiently large or include an accumulator bin (not shown) for the web after the oven. Web 10, after leaving treatment unit 380e, can either be wound onto a spool 460 for later use by driving web 10 therefrom serially through multiple application stations each of which includes a print head 210, or it may be driven directly from treatment unit 380 sequentially through such application stations. Both options are illustrated in FIG. 11. Methods of providing polylysine or other suitable coatings are described, for example, in U.S. Pat. No. 6,077,674 and the references cited therein. Rather than using the roller 42 configuration in FIG. 5 on both sides of the drop deposition location 212 to restrain the web from movement in the direction of axis 202, there is instead used a pair of fixed edge guides 426 above a support in the form of block 450. Block 450 may have a cross-section similar in appearance to shoulders 46 and intermediate section 48 as shown in FIG. 5, such that block 450 will only contact back surface 11b of web 10 along opposite edge margins while not contacting the central portion of the web intermediate the edge margins. In an alternative second construction though, block 450 may contact the entire width of web 10 across back surface 11b immediately opposite each location 212. While both configurations of block 450 support web 10 at the drop deposition locations 212, only the second construction supports the web across each entire drop deposition location 212. Guides of the pair of edge guides 426 contact respective opposite edge margins 13a, 13b along front surface 11a of web 10, while not contacting the central portion of the web intermediate the edge margins (which central portion carries arrays 12). A pair of guides 426 is positioned on each side of drop deposition location 212 beneath each head 210. In this manner, the web 10 is restrained on either side of each location 212 by the contact of guides 426 on front surface 11a, and by the simultaneous contact of block 450 on the back surface 11b opposite guides 426, from moving in the direction of axis 202 at locations 212. Of course, block 450 could be replaced by a roller 42a at each location 212 with rollers 42a, 42c positioned on respective sides of each location 21, in a manner similar to that shown in FIG. 4 (using either solid cylindrical rollers or rollers of construction shown in FIG. 5. Guides 426 could at the same time also be replaced by rollers 42. Each head 210 deposits one or multiple different polynucleotide compositions at respective features, with their being sufficient heads 210 to complete the fabrication of all arrays 212. Again, each head may be independently controlled by processor 140.

After leaving the last head 210, web 10 may then be wound on spool 480 for later use or may be driven directly to a stabilizing block 490, both options being illustrated in FIG. 11. At stabilizing block 490 web 10 passes in sequence through: ultraviolet treatment station 380 to cross-link deposited polynucleotides to surface 11a; (alternatively, the cross-linking can be accomplished by heating.) NaOH and N-methylpyridine reagent baths 384k, 384m, respectively, in order to block non-specific binding sites on surface 11a; then water, hot-water, and ethanol wash baths 386m, 386p, and 386q, respectively. Polylysine or other coatings and cross-linking are further described in U.S. Pat. No. 6,284,465 and the references cited therein with respect to these techniques. Web 10 with fabricated arrays 12 may then be wound on spool 430b or sent to cutter 152, then forwarded as described in connection with the operation of the apparatus of FIG. 4.

Figure 12:
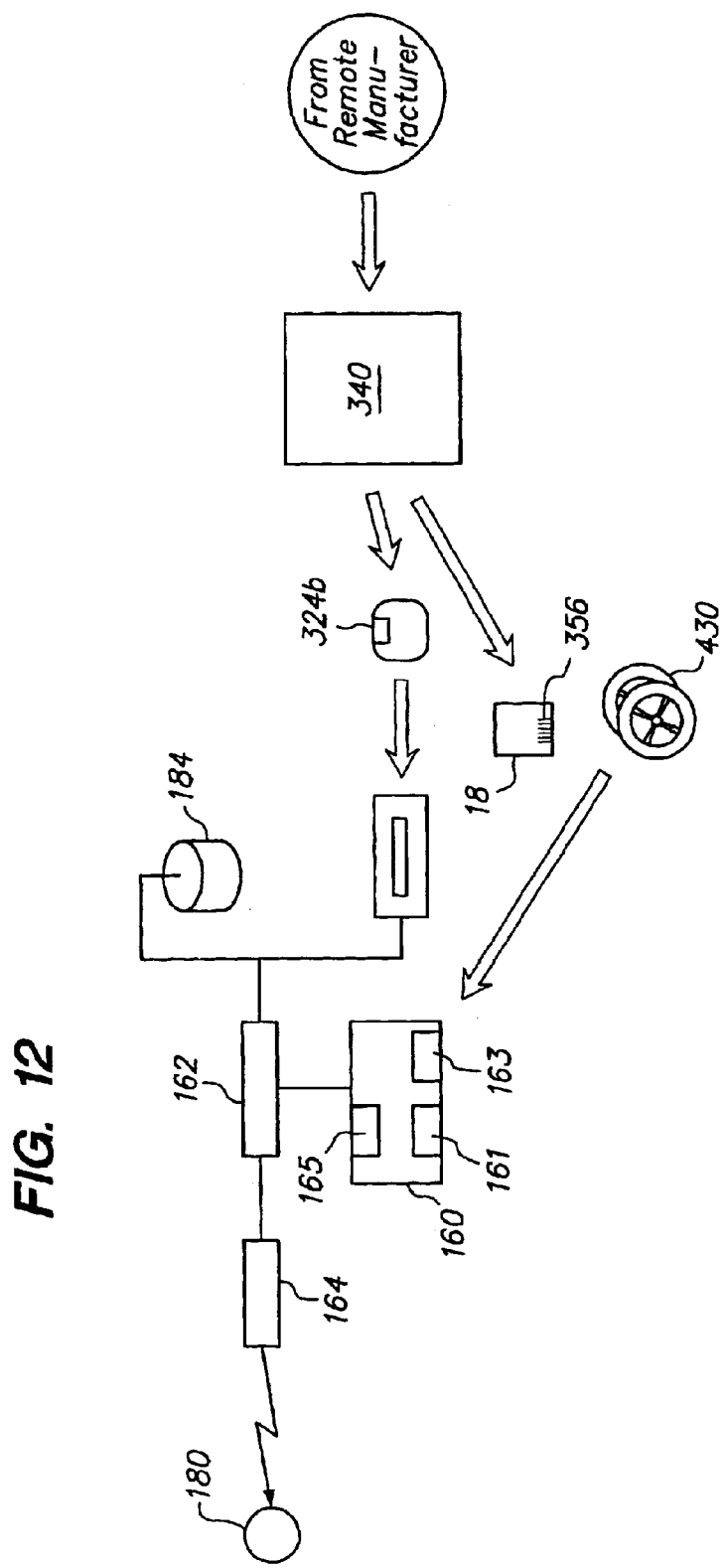
FIG. 12 illustrates a user station at which fabricated arrays of the present invention may be used.

FIG. 12 illustrates an apparatus for receiving an addressable array 12, in particular a single "user station", which likely to be (but not necessarily) remote from the fabrication station of FIG. 4 (usually the user station is at the location of the customer which ordered the received array 12). The user station includes a processor 162, a memory 184, a scanner 160 which can read an array, data writer/reader 186 (which may be capable of writing/reading to the same type of media as writer/reader 320), and a communication module 164 which also has access to communication channel 180. Scanner 160 may include a holder 161 which receives and holds an array assembly in the form of an array unit 18 or in the form of web 10 carrying arrays 12, as well as a source of illumination (such as a laser) and a light sensor 165 to read fluorescent light signals from respective features on the array. Communication module 164 may be any type of suitable communication module, such as those described in connection with communication module 144. Memory 184 can be any type of memory such as those used for memory 141. Scanner 160 can be any suitable apparatus for reading an array, such as one which can read the location and intensity of fluorescence at each feature of an array following exposure to a fluorescently labeled sample. For example, such a scanner may be similar to the DNA MICROARRAY SCANNER available from Agilent Technologies, Inc. Palo Alto, Calif. Other suitable apparatus and methods are described in U.S. patent applications: Ser. No. 09/846,125 "Reading Multi-Featured Arrays" by Dorsel et al.; and Ser. No. 09/430,214 "Interrogating Multi-Featured Arrays" by Dorsel et al. Scanner 160 also includes a reader 163 to read a bar code 356 appearing on segment 18. The scanning components of scanner 160, holder 161, and reader 163 may all be contained within the same housing of a single same apparatus.

Figure 13:
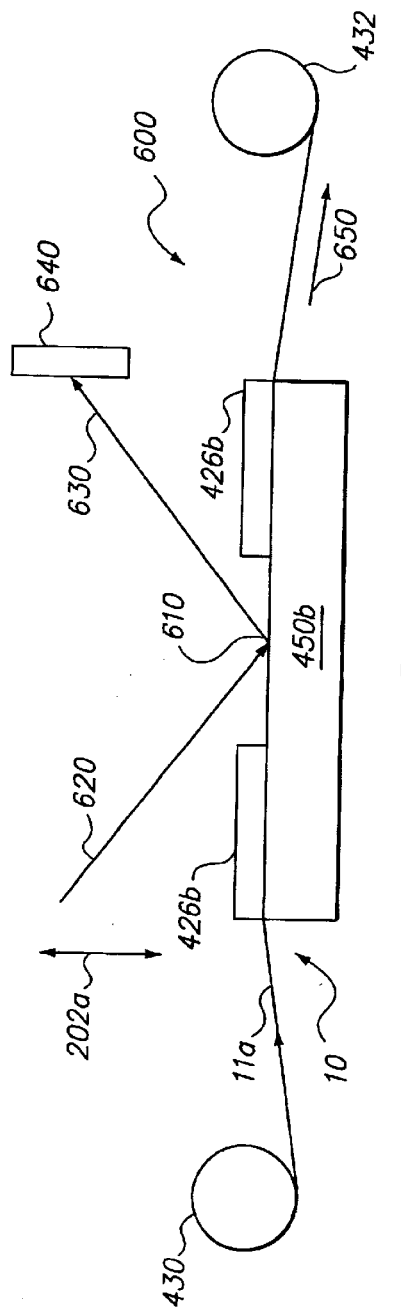
FIG. 13 is a side view of a reading station portion of a scanner present in the user station of FIG. 10.
Figure 14:
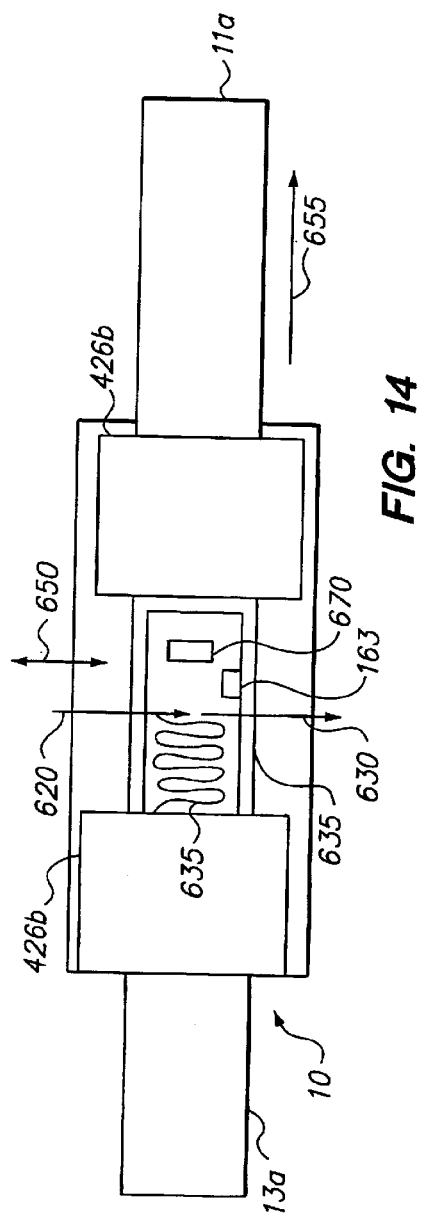
FIG. 14 is atop view of the portion illustrated in FIG. 13.
Figure 15:
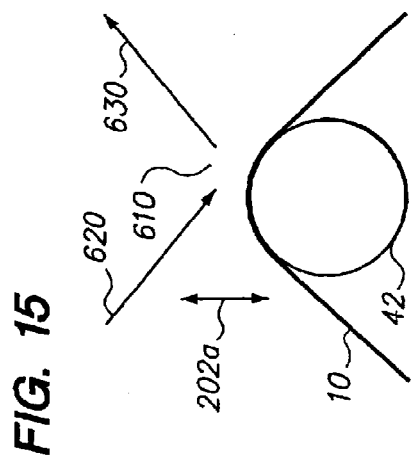
FIG. 15 is a side view of a reading station portion of an alternate embodiment.

When scanner 160 is intended to receive a web 10 of arrays, the holder may be constructed as illustrated in FIGS. 13 and 14. In FIGS. 13 and 14 a transport system is provided which includes a support in the form of block 450b, a pair of opposed edge guides 426b, and a motor (not shown) on output reel 432, such that the web can be driven in a lengthwise direction past a reading location, specifically detecting location 610. Block 450b and edge guides 426b are of similar construction to block 450 and edge guides 426 discussed above in connection with FIG. 11. Alternatively, block 450 and guides 426 could be replaced with just one roller 42 (either cylindrical or of FIG. 5 construction) in a manner shown in connection with FIG. 15. In the configuration of FIG. 15 web 10 is supported at a position immediately opposite the detection location 610 by being bent over a roller so as to maintain a linear region in the form of a line of scanning, flat against the roller 42. In the particular arrangement of FIG. 15, detecting location 610 is located and moved along a line positioned mid-way of the circumference portion of roller 42 contacted by web 10, and parallel to the axis of rotation of roller 42. Web 10 can be bent such that the angle between an input and output portion of web 10 on either side of roller 42 is at least five, or at least ten, or at least twenty, or even at least thirty degrees. In a further alternative, block 450 and guides 426 could be replaced with multiple rollers in any of the manners as described in connection with FIG. 11, although a circular cross-section cylindrical roller 42 would then contact back side 11a immediately opposite each detecting location 610 in a manner similar to roller 42b in FIG. 4. In any event, either block 450 or a roller 42 would support the web at detecting location 610 and restrain the web 10 from movement in the direction of axis 202a, while guides 426 (or other rollers 42 which replace them), if present, serve to further restrain the web from movement in the direction of axis 202a and so assist in maintaining web 10 flat while at detecting location 610. A light source such as a laser illuminates location 610 with beam 620, and any resulting fluorescence 630 from features 16 at detecting location 610, is detected at fluorescence detector 640. Detecting location 610 is moved back and forth across web 10 in the direction of axis 650 while web 10 is driven past detecting location in the direction 655, resulting in a scanned pattern illustrated at 635.

The foregoing description relates to a scanner which reads the array by detecting an optical characteristic of the features 16, such as fluorescence which is dependent upon an amount of a sample component that may have bound to features 16 after exposing arrays 12 to samples tagged with fluorescent labels. However, other characteristics of features 16 may be read instead. For example, where the arrays are exposed to samples tagged with magnetically readable labels, the detector could be in the form of a head 670 which detects a magnetic characteristic of the features such as changing magnetic field. Magnetically readable labels in such a case may include any label which generates or affects a magnetic field in a detectable way.

A user station may also be provided with an apparatus 540 for exposing arrays 12 on web 10 to a sample such as shown in FIGS. 14 and 15. Such apparatus includes a cylindrical member 550 with a series of chambers 560 each having an opening 564 in the form of an open face, with openings 564 being arranged in a helical format on the surface of cylindrical member 550. An inlet conduit 566 communicates with a rear side of each chamber 560 and hence with opening face 564, as well as with a main conduit 565. Each main conduit 565 communicates through conduits 566 with a line of chambers 560. Conduits (not shown) parallel to each shown conduit 565 and 560, connected in a same fashion but to a front side of each chamber 560, may also be provided for venting or other outlet. Openings 564 can seal against web 10 about respective arrays 12 when web 10 is curved to wind in a helical format about member 550 as illustrated in FIG. 146 To assist in such sealing a sealing ring (not shown) can be attached to member 550 about each opening 564. Web 10 then closes off and helps define chambers 560. Suitable clips or other means (such as pins for engaging in perforations in web 10, not shown) can be provided to retain web 10 in the mounted position of FIG. 17.

It will be understood that there may be multiple user stations such as shown in FIG. 12, each remote from the fabrication station and each other, in which case the fabrication station acts as a central fabrication station (that is, a fabrication station which services more than one remote user station at the same or different times). One or more such user stations may be in communication with the fabrication station at any given time. It will also be appreciated that processors 140 and 162 can be programmed from any computer readable medium carrying a suitable computer program. For example, such a medium can be any memory device such as those described in connection with memory 141, and may be read locally (such as by reader/writer 320 in the case of processor 140 or writer/reader 186 in the case of processor 162) or from a remote location through communication channel 180.

The operation of the fabrication station will now be described. It will be assumed that a web 10 on which arrays 12 are to be fabricated, is in position as illustrated in FIG. 4 and that processor 140 is programmed with the necessary layout information to fabricate target arrays 12. For each array 12 to be fabricated, processor 140 will generate a corresponding unique identifier which may be stored in memory 141 in association with data on one or more characteristics of features 16 of the same array 12. Generation of such an identifier and feature characteristic data (in the form of array layout data) and their use are described, for example, in U.S. Pat. No. 6,180,351. Alternatively or additionally, such feature characteristic data and associated identifier for one or more arrays 12 which are to be shipped to a same customer, can be stored onto a portable storage medium 324b by writer/reader 326 for provision to the remote customer. Processor 140 controls fabrication of an array 12, by depositing one or more drops of each biopolymer or precursor unit onto a corresponding location of a feature 16 on web 10 so as to fabricate the arrays 12 in the manner described above. The deposited drops may contain one or more biopolymer or precursor unit depending on the feature composition desired. Where an activator is required (such as for phosphoramidites in the in situ method) this may provided in the same or different drops as the component requiring activation. Note that with any of the configurations of FIGS. 8 to 11 tedious removal of a substrate from beneath a head 210 and placement into a reagent or wash bath, and possible replacement under one or more heads (in the case of the in situ method), is avoided by using web 10 rather than individual substrates.

Either before array fabrication on web 10 has been commenced, or after it has been completed, web 10 may be sent to writer 150 which, under control of processor 140, writes the identifier 356 for each array 12 in the form of bar codes 356 onto web 10 each in association with its corresponding array (by being physically close to it in the manner shown in FIG. 1). The web 10 may then be sent to a cutter 152 wherein portions of web 10 carrying an individual array 12 and its associated local identifier 356 are separated from the remainder of web 10, to provide multiple array units 18. Alternatively, as mentioned above, the web 10 carrying the fabricated arrays 12 can be wound onto reel 430. The array unit 18 or reel 430 is placed in package 340 along with storage medium 324b (if used) carrying at least the feature characteristic data and identifier for the same array unit 18 or arrays 12 on reel 430 (and possibly for other array 12 which are to be sent to the same remote customer location), and the package then shipped to a remote user station.

The above sequence can be repeated at the fabrication station as desired for multiple webs 10 in turn. As mentioned above, the fabrication station may act as a central fabrication station for each of multiple remote user stations, in the same manner as described above. Whether or not the fabrication station acts as a central fabrication station, it can optionally maintain a database of unique map identifiers in memory 141, each in association with the corresponding feature characteristic data.

Figure 16:
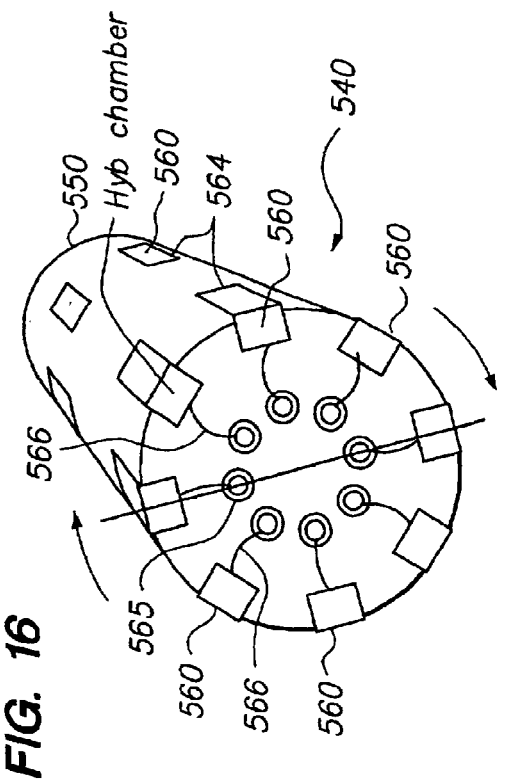
FIG. 16 is a perspective view of a portion of a hybridization apparatus with which fabricated arrays of the present invention may be used, as viewed from the perspective of line 16—16 of FIG. 17.
Figure 17:
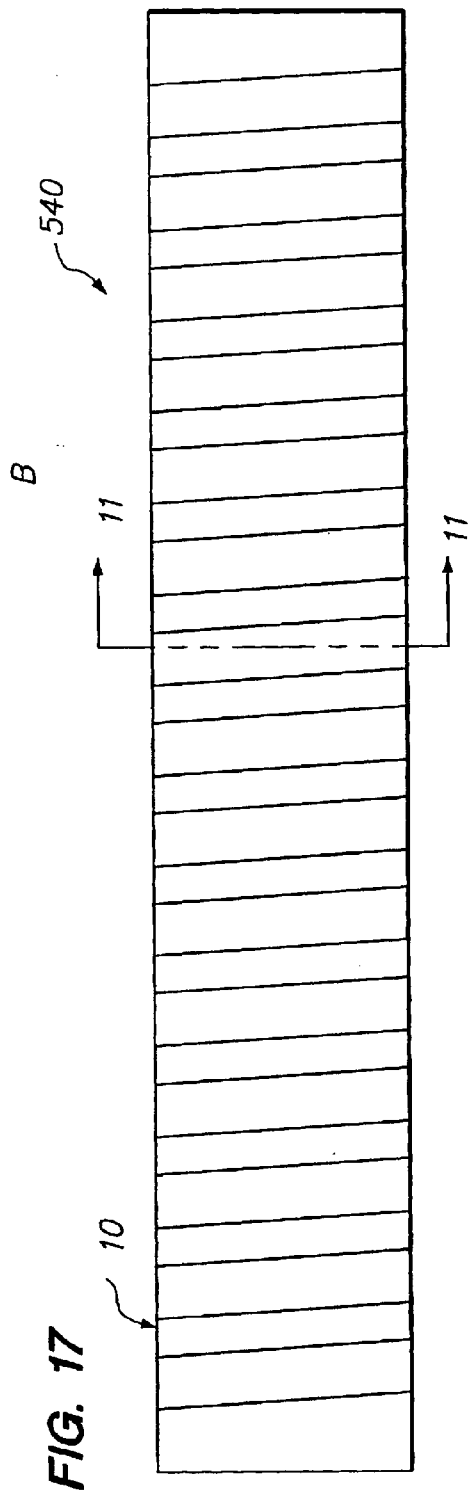
FIG. 17 is a side view of the apparatus of FIG. 16.

At the user station of FIG. 12, the resulting package 340 is then received from the remote fabrication station. A sample, for example a test sample, is exposed to the array 12 on the array unit 18 received in package 340 Alternatively if a reel 430 is received, the arrays thereon may be simultaneously hybridized with the same or different samples using an apparatus such as that of FIGS. 16 and 17. Note that when an apparatus of FIGS. 16, 17 is used, each array 12 is exposed to its own continuous volume of a sample fluid. As an alternative to the apparatus of FIGS. 16 and 17, the web 10 may simply be dunked or placed into a tank containing the sample provided such a large volume of sample is available. For example, web 10 may be wound in a spiral and placed in a tube and sample moved back and forth within the tube. Whatever apparatus is used for hybridization, fiducial marks 15 or identifiers 356 may be used to ascertain the position of the arrays 12 on web 10 so that they can be properly aligned completely inside the hybridization chamber (either visually or by a detector which detects their position and aligns the arrays 12 in their hybridization chambers based on the detected fiducials or identifiers). In an alternative hybridization arrangement, with individual units 18, the substrate could be folded back on itself (or onto a part of substrate 10 not carrying an array 12 when the areas 17 between arrays separated in the lengthwise direction of web 10 are at least equal to the length of arrays 12 in that direction). The perimeter may then be sealed to form a closed packet, with a sample being introduced before or after (for example, by a syringe) such folding and sealing. Fluid mixing and within such a formed packed could be accomplished by passing the packet through one or more rollers, which would also distribute the sample over all elements of an array 12. Following hybridization and washing in a known manner, the array unit 18 is then inserted into holder 161 in scanner 160 and read by it to obtain read results (such as information representing the fluorescence pattern on the array 12). Alternatively, for a received reel 430 the arrays can be read using a scanner with the components of FIGS. 13 and 14. The reader 163 in scanner 160 also reads the identifier 356 present on the array units 18 or web 10 in association with the corresponding array 12, while the array unit 18 is still positioned in retained in holder 161 or as the identifiers 356 pass beneath reader 163 as shown in FIG. 14. Using identifier 356, processor 162 may then retrieve the characteristic data for the corresponding array 12 from portable storage medium 324b or from the database of such information in memory 141 by communicating the map identifier to that database through communication module 164 and communication channel 180 and receiving the corresponding identity map in response. In the latter situation, processor 162 may obtain the communication address of communication module 144 by which to access memory 141 (or the address of another database carrying the identity map and associated identifier of array 12), from the communication address in identifier 356.

The resulting retrieved characteristic data for an array may be used to either control reading of the array or to process information obtained from reading the array. For example, the customer may decide (through providing suitable instructions to processor 162) that a particular feature need not be read or the data from reading that feature may be discarded, since the polynucleotide sequence at that feature is not likely to produce any reliable data under the conditions of a particular sample hybridization. Results from the array reading can be processed results, such as obtained by rejecting a reading for a feature which is below a predetermined threshold and/or forming conclusions based on the pattern read from the array (such as whether or not a particular target sequence may have been present in the sample). The results of the interrogation (processed or not) can be forwarded (such as by communication) to be received at a remote location for further evaluation and/or processing, or use, using communication channel 180 or reader/writer 186 and medium 190. This data may be transmitted by others as required to reach the remote location, or re-transmitted to elsewhere as desired.

In a variation of the above, it is possible that each array unit 18 may be contained with a suitable housing. Such a housing may include a closed chamber accessible through one or more ports normally closed by septa, which carries the web 10. In this case, the identifier for each array may be applied to the housing. Also, instead of using rollers such as those of FIG. 5 in the situations mentioned above, one might instead use as a roller two axially aligned sprockets when edge margins 13a, 13b of web 10 have suitable perforations to accommodate such sprockets.

Note that the order of the steps in methods of the present invention may be varied where logically possible. It will also be appreciated that multiple arrays on web 10 may have same in that they have the features of the same composition arranged in the same manner. In such a case, if a customer uses the same arrays it may simply obtain at least some of the characteristic data (such as the location and composition of each feature) for those same arrays just once. This common part of the characteristic data for those arrays could be provided in magnetically or optically (for example, one or more bar codes) encoded format on a leader portion of web 10. Any specific data relating to a given array 12 (for example, an error in a feature, such as incorrect feature size, placement, or composition) could still be obtained or retrieved using identifier 356. This would avoid having to retrieve common characteristic data multiple times.

Modifications in the particular embodiments described above are, of course, possible. For example, where a pattern of arrays is desired, any of a variety of geometries may be constructed other than the organized rows and columns of arrays 12 of FIG. 1. For example, arrays 12 can be arranged in a series of curvilinear rows across the substrate surface (for example, a series of concentric circles or semi-circles of spots), and the like. Similarly, the pattern of regions 16 may be varied from the organized rows and columns of features in FIG. 2 to include, for example, a series of curvilinear rows across the substrate surface(for example, a series of concentric circles or semi-circles of spots), and the like. Even irregular arrangements of the arrays or the regions within them can be used. However, the user should be provided with some means (for example, through the array identifier) of being able to ascertain at least some characteristics of the features (for example, any one or more of feature composition, location, size, performance characteristics in terms of significance in variations of binding patterns with different samples, or the like). The configuration of the array may be selected according to manufacturing, handling, and use considerations. The present methods and apparatus may be used to fabricate and use arrays of other biopolymers, polymers, or other moieties on surfaces in a manner analogous to those described above. Accordingly, reference to polymers can often be replaced with reference to "chemical moieties".

Various further modifications to the particular embodiments described above are, of course, possible. Accordingly, the present invention is not limited to the particular embodiments described in detail above.

What is claimed is:

1. A method of forming arrays of polymers each having a pattern of features on a surface of a flexible elongated web, comprising:
    (a) at an application station, applying the polymers or their precursor units to the surface;
    (b) at a reagent station, covering multiple features with a continuous volume of reagent which chemically reacts with precursors or the web;
    (c) driving the flexible elongated web in a lengthwise direction through the application station; and
    (d) repeating (a) through (c) as needed to form the arrays along the web.

2. A method of forming arrays of polymers each having a pattern of features on a surface of a flexible elongated web, comprising:
    (a) at an application station, applying the polymers or their precursor units to the surface;
    (b) at a reagent station, covering multiple features with a continuous volume of reagent which chemically reacts with precursors or the web;
    (c) driving the flexible elongated web in a lengthwise direction through the application and reagent stations; and
    (d) repeating (a) through (c) as needed to form the arrays along the web.

3. A method according to claim 1 wherein the application station is a drop deposition station at which drops containing the polymers or their precursor units are deposited on the web.

4. A method according to claim 2 wherein the application station is a drop deposition station at which drops containing the polymers or their precursor units are deposited on the web.

5. A method according to claim 2 wherein the polymers are DNA.

6. A method according to claim 2 wherein the reagent station of step (b) comprises a reagent bath through which the web is driven.

7. A method according to claim 4 additionally comprising restraining the web on both surfaces on either side of the drop deposition station to assist in maintaining the web flat while in the drop deposition station.

8. A method according to claim 2 wherein the web is driven through a same or different reagent stations such that (b) is repeated on each of multiple surface regions of the web.

9. A method according to claim 8 wherein (b) is repeated with a same surface region of the web passing through different reagent stations.

10. A method according to claim 2 wherein the web is driven through multiple application and reagent stations.

11. A method according to claim 2 wherein at least some of the repetitions of (a) occur simultaneously on different array regions at respective different application stations.

12. A method according to claim 11 wherein: precursor units are applied in (a); and the web is driven through a reagent station between application stations.

13. A method according to claim 2 wherein the web is driven through multiple application stations without an intervening reagent station, and then through a reagent station.

14. A method according to claim 13 wherein the polymers are applied at the application station.

15. A method according to claim 14 wherein the polymers are biopolymers.

16. A method according to claim 10 wherein the web is driven in a continuous loop through a same application station and a same reagent station.

17. A method according to claim 2 additionally comprising driving the web through a wash station at which the web is exposed to a wash fluid.

18. A method according to claim 17 wherein the web is driven through a reagent station and a wash station after being driven through an application station, and is then driven through an application station.

19. A method according to claim 10 wherein after being driven through an application station the web is driven through multiple reagent stations and is then driven through an application station.

20. A method according to claim 9 wherein the web is driven in different directions between at least two of the reagent stations.

21. A method according to claim 2 wherein the polymers are biopolymers.

22. A method of forming arrays of polymers each having a pattern of features on a surface of a flexible elongated web, comprising:
(a) at drop deposition station, applying a drop containing a polymer precursor unit at each feature location on the web surface so as to become linked thereto;
(b) at a reagent station, covering multiple features with a continuous volume of reagent which chemically reacts with the units;
(c) driving the flexible elongated web in a lengthwise direction through the application and reagent stations; and
(d) repeating (a) through (c) as needed so as to form the arrays, wherein at each feature a unit deposited in one cycle becomes linked with a unit deposited in a subsequent cycle.

23. A method according to claim 22 wherein the reagent deprotects a protected linking group of a unit deposited in a same cycle so that a unit deposited in a next cycle can link with the deprotected unit deposited in the preceding cycle.

24. A method according to claim 22 wherein the reagent comprises an oxidizing agent.

25. A method according to claim 22 wherein: the array is a polynucleotide array; the drop deposition station deposits drops containing nucleoside phosphoramidites; and the reagent comprises at least one of a reagent for deprotecting protected phosphoramidites or an oxidation reagent which oxidizes internucleoside phosphite bonds to phosphate bonds.

26. A method according to claim 25 additionally comprising driving the web lengthwise through a wash station following a reagent station, at which wash station multiple features are covered with a continuous volume of wash fluid.

27. A method according to claim 26 wherein the wash station is a wash bath.

28. A method according to claim 22 wherein the web is driven through multiple deposition stations and multiple reagent stations.

29. A method according to claim 22 wherein the web is driven sequentially through multiple reagent stations between different application stations.

30. A method according to claim 22 wherein the web is driven in different directions between at least two different reagent stations.

31. A method of forming arrays of biopolymers each having a pattern of features on a surface of a flexible elongated web, comprising:
(a) at an application station, applying the biopolymers or their precursor units to the surface;
(b) at a reagent station, contacted the web with a reagent which chemically reacts with the precursors or the web;
(c) driving the flexible elongated web through the application and reagent stations, wherein the web is driven in different directions between an input side of the application station and an output side of the reagent station; and (d) repeating (a) through (c) as needed to form the arrays along the web.

32. A method according to claim 31 wherein the application station is a drop deposition station at which drops containing the biopolymers moieties or their precursor units are deposited on the web.

33. A method according to claim 32 wherein: precursor units are applied at the application station; and the web is driven through a reagent station between application stations.

34. A method according to claim 32 wherein: the polymers are polynucleotides; and the web is driven through multiple drop deposition stations and multiple reagent stations; the method additionally comprising driving the web through a wash station at which at which multiple features are covered with a continuous volume of wash fluid.

35. A method according to claim 34 wherein the web is driven through a reagent station followed by a wash station, between successive deposition stations.

36. A method of forming arrays of polymers each having a pattern of features on a surface of a flexible elongated web, comprising:
(a) at an application station, applying the polymers or their precursor units to the surface;
(b) at a reagent station, covering multiple features with a continuous volume of reagent which chemically reacts with precursors or the web;
(c) driving the flexible elongated web in a lengthwise direction through the application station and reagent stations; and
(d) repeating (a) through (c) as needed to form the arrays along the web; wherein the web is directed in a path by one or more guides each contacting a web surface along opposite edge margins while not contacting a central portion of the web intermediate the edge margins.

37. A method according to claim 36 wherein the guides rotate and contact edge margins of the web surface carrying the arrays.

38. A method of preparing a surface of a flexible elongated web to receive a biopolymer array, comprising driving the web in a lengthwise direction from a supply reel and successively through multiple surface treatment stations so as to provide a linking layer bound to the surface which layer has a polynucleotide, protein, nucleoside or amino acid minimum binding affinity of $10^4$ to $10^6$ units/$\mu^2$.

39. A method according to claim 38 wherein the linking layer is less than 10 angstroms thick.

40. A method according to claim 38 wherein the linking layer comprises any one or more of polylysine, an aldehyde, an amine, or a thiol.

41. A method according to claim 38 wherein the linking layer comprises a silane.

42. A method according to claim 41 wherein the silane has a free amino group.

43. A method according to claim 38 wherein the linking layer comprises a mixture of different silanes.

* * * * *